United States Patent
Braido et al.

(10) Patent No.: US 10,010,410 B2
(45) Date of Patent: Jul. 3, 2018

(54) COLLAPSIBLE AND RE-EXPANDABLE PROSTHETIC HEART VALVE CUFF DESIGNS AND COMPLEMENTARY TECHNOLOGICAL APPLICATIONS

(71) Applicant: St. Jude Medical, LLC, Abbott Park, IL (US)

(72) Inventors: Peter Nicholas Braido, Wyoming, MN (US); Paul Edward Ashworth, Wyoming, MN (US); Julia Ann Schraut, Shoreview, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 0 days.

(21) Appl. No.: 13/938,618

(22) Filed: Jul. 10, 2013

(65) Prior Publication Data
US 2013/0338765 A1    Dec. 19, 2013

Related U.S. Application Data

(62) Division of application No. 12/737,256, filed as application No. PCT/US2009/004094 on Jul. 15, 2009, now Pat. No. 8,808,356.

(Continued)

(51) Int. Cl.
*A61F 2/24*    (2006.01)
*A61F 2/01*    (2006.01)

(52) U.S. Cl.
CPC ............. *A61F 2/2409* (2013.01); *A61F 2/01* (2013.01); *A61F 2/243* (2013.01); *A61F 2/246* (2013.01);

(Continued)

(58) Field of Classification Search
CPC ................ A61F 2/06; A61F 2/24; A61F 2/82
(Continued)

(56) References Cited

U.S. PATENT DOCUMENTS 3,409,013 A    11/1968 Berry
3,467,102 A    9/1969 Fogarty et al.
(Continued)

FOREIGN PATENT DOCUMENTS

CA    2571047 A1    1/2006
DE    2246526    3/1973
(Continued)

OTHER PUBLICATIONS

Extended European Search Report for Application No. 14180622.4 dated Nov. 21, 2014.
(Continued)

*Primary Examiner* — Matthew Schall
(74) *Attorney, Agent, or Firm* — Lerner, David, Littenberg, Krumholz & Mentlik, LLP

(57) ABSTRACT

A prosthetic heart valve is provided with a cuff having features which promote sealing with the native tissues even where the native tissues are irregular. The cuff may include a portion adapted to bear on the LVOT when the valve is implanted in a native aortic valve. The valve may include elements for biasing the cuff outwardly with respect to the stent body when the stent body is in an expanded condition. The cuff may have portions of different thickness distributed around the circumference of the valve in a pattern matching the shape of the opening defined by the native tissue. All or part of the cuff may be movable relative to the stent during implantation.

6 Claims, 17 Drawing Sheets

Related U.S. Application Data

(60) Provisional application No. 61/134,995, filed on Jul. 15, 2008.

(52) U.S. Cl.
CPC .......... *A61F 2/2412* (2013.01); *A61F 2/2418* (2013.01); *A61F 2/2433* (2013.01); *A61F 2/2436* (2013.01); *A61F 2/2442* (2013.01); *A61F 2/2466* (2013.01); *A61F 2220/0008* (2013.01); *A61F 2220/0075* (2013.01); *A61F 2230/0054* (2013.01); *A61F 2230/0069* (2013.01); *A61F 2250/0039* (2013.01); *A61F 2250/0069* (2013.01)

(58) Field of Classification Search
USPC ....................................................... 623/1.26
See application file for complete search history.

(56) References Cited

U.S. PATENT DOCUMENTS

| | | |
|---|---|---|
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,983,581 A | 10/1976 | Angell et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,275,469 A | 6/1981 | Gabbay |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,491,986 A | 1/1985 | Gabbay |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goeme et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,258,023 A | 11/1993 | Reger |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,423 A | 1/1996 | Ravenscroft et al. |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,607,470 A | 3/1997 | Milo |
| 5,609,626 A | 3/1997 | Quijano et al. |
| 5,628,786 A | 5/1997 | Banas et al. |
| 5,639,274 A | 6/1997 | Fischell et al. |
| 5,665,115 A | 9/1997 | Cragg |
| 5,693,088 A | 12/1997 | Lazarus |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,769,882 A | 6/1998 | Fogarty et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,843,167 A | 12/1998 | Dwyer et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,928,281 A | 7/1999 | Huynh et al. |
| 5,935,163 A | 8/1999 | Gabbay |
| 5,957,949 A | 9/1999 | Leonhardt et al. |
| 5,961,549 A | 10/1999 | Nguyen et al. |
| 6,015,431 A | 1/2000 | Thornton et al. |
| 6,027,525 A | 2/2000 | Suh et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,110,198 A | 8/2000 | Fogarty et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,214,036 B1 | 4/2001 | Letendre et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,264,691 B1 | 7/2001 | Gabbay |
| 6,267,783 B1 | 7/2001 | Letendre et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,312,465 B1 | 11/2001 | Griffin et al. |
| 6,350,277 B1 | 2/2002 | Kocur |
| 6,352,554 B2 | 3/2002 | De Paulis |
| 6,368,348 B1 | 4/2002 | Gabbay |
| 6,419,695 B1 | 7/2002 | Gabbay |

(56) References Cited

U.S. PATENT DOCUMENTS

| | | |
|---|---|---|
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,702 B1 | 12/2002 | Besselink |
| 6,488,704 B1 | 12/2002 | Connelly et al. |
| 6,517,576 B2 | 2/2003 | Gabbay |
| 6,533,810 B2 | 3/2003 | Hankh et al. |
| 6,569,196 B1 | 5/2003 | Vesely |
| 6,582,464 B2 | 6/2003 | Gabbay |
| 6,605,112 B1 | 8/2003 | Moll et al. |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,780,510 B2 | 8/2004 | Ogle et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,814,754 B2 | 11/2004 | Greenhalgh |
| 6,830,584 B1 | 12/2004 | Seguin |
| 6,837,902 B2 | 1/2005 | Nguyen et al. |
| 6,860,901 B1 | 3/2005 | Baker et al. |
| 6,869,444 B2 | 3/2005 | Gabbay |
| 6,893,460 B2 | 5/2005 | Spenser et al. |
| 6,908,481 B2 | 6/2005 | Cribier |
| 6,911,040 B2 | 6/2005 | Johnson et al. |
| 6,951,573 B1 | 10/2005 | Dilling |
| 7,018,406 B2 | 3/2006 | Seguin et al. |
| 7,025,780 B2 | 4/2006 | Gabbay |
| 7,101,396 B2 | 9/2006 | Artof et al. |
| 7,137,184 B2 | 11/2006 | Schreck |
| 7,147,663 B1 | 12/2006 | Berg et al. |
| 7,160,322 B2 | 1/2007 | Gabbay |
| 7,195,641 B2 | 3/2007 | Palmaz et al. |
| 7,247,167 B2 | 7/2007 | Gabbay |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,571 B2 | 5/2008 | Pease et al. |
| 7,374,573 B2 | 5/2008 | Gabbay |
| 7,381,218 B2 | 6/2008 | Schreck |
| 7,381,219 B2 | 6/2008 | Salahieh et al. |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,462,191 B2 | 12/2008 | Spenser et al. |
| 7,481,838 B2 | 1/2009 | Carpentier et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,597,711 B2 | 10/2009 | Drews et al. |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,871,435 B2 | 1/2011 | Carpentier et al. |
| 7,892,281 B2 | 2/2011 | Seguin et al. |
| 7,914,569 B2 | 3/2011 | Nguyen et al. |
| 7,951,197 B2 | 5/2011 | Lane et al. |
| 7,959,666 B2 | 6/2011 | Salahieh et al. |
| 7,959,672 B2 | 6/2011 | Salahieh et al. |
| 7,959,674 B2 | 6/2011 | Shu et al. |
| 7,967,857 B2 | 6/2011 | Lane |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| 8,083,793 B2 | 12/2011 | Lane et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,226,710 B2 | 7/2012 | Nguyen et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,349,000 B2 | 1/2013 | Schreck |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,685 B2 | 6/2013 | Hariton et al. |
| 8,454,686 B2 | 6/2013 | Alkhatib |
| 8,500,798 B2 | 8/2013 | Rowe et al. |
| 8,512,396 B2 | 8/2013 | Styrc |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,673,000 B2 | 3/2014 | Tabor et al. |
| 8,685,080 B2 | 4/2014 | White |

(56) References Cited

U.S. PATENT DOCUMENTS

| | | |
|---|---|---|
| 8,728,154 B2 | 5/2014 | Alkhatib |
| 8,747,459 B2 | 6/2014 | Nguyen et al. |
| 8,747,460 B2 | 6/2014 | Tuval et al. |
| 8,764,820 B2 | 7/2014 | Dehdashtian et al. |
| 8,771,345 B2 | 7/2014 | Tuval et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,845,721 B2 | 9/2014 | Braido et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 8,992,608 B2 | 3/2015 | Haug et al. |
| 9,393,110 B2 | 7/2016 | Levi et al. |
| 2001/0021872 A1 | 9/2001 | Bailey et al. |
| 2001/0027338 A1 | 10/2001 | Greenberg |
| 2001/0041928 A1 | 11/2001 | Pavcnik et al. |
| 2002/0032481 A1 | 3/2002 | Gabbay |
| 2002/0036220 A1 | 3/2002 | Gabbay |
| 2002/0055774 A1 | 5/2002 | Liddicoat |
| 2002/0173842 A1 | 11/2002 | Buchanan |
| 2003/0023303 A1 | 1/2003 | Palmaz et al. |
| 2003/0040792 A1 | 2/2003 | Gabbay |
| 2003/0050694 A1 | 3/2003 | Yang et al. |
| 2003/0100939 A1 | 5/2003 | Yodfat et al. |
| 2003/0114913 A1 | 6/2003 | Spenser et al. |
| 2003/0130726 A1 | 7/2003 | Thorpe et al. |
| 2003/0212454 A1 | 11/2003 | Scott et al. |
| 2003/0236567 A1 | 12/2003 | Elliot |
| 2003/0236568 A1 | 12/2003 | Hojeibane et al. |
| 2004/0033364 A1 | 2/2004 | Spiridigliozzi et al. |
| 2004/0039436 A1 | 2/2004 | Spenser et al. |
| 2004/0049262 A1 | 3/2004 | Obermiller et al. |
| 2004/0082989 A1 | 4/2004 | Cook et al. |
| 2004/0093075 A1 | 5/2004 | Kuehne |
| 2004/0111111 A1 | 6/2004 | Lin |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0075718 A1 | 4/2005 | Nguyen et al. |
| 2005/0075725 A1 | 4/2005 | Rowe |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0234546 A1 | 10/2005 | Nugent et al. |
| 2005/0256566 A1 | 11/2005 | Gabbay |
| 2005/0283231 A1 | 12/2005 | Haug et al. |
| 2006/0004442 A1 | 1/2006 | Spenser et al. |
| 2006/0008497 A1 | 1/2006 | Gabbay |
| 2006/0025855 A1 | 2/2006 | Lashinski et al. |
| 2006/0025857 A1 | 2/2006 | Bergheim et al. |
| 2006/0074484 A1 | 4/2006 | Huber |
| 2006/0122692 A1 | 6/2006 | Gilad et al. |
| 2006/0149350 A1 | 7/2006 | Patel et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195186 A1 | 8/2006 | Drews et al. |
| 2006/0206202 A1 | 9/2006 | Bonhoeffer et al. |
| 2006/0229719 A1 | 10/2006 | Marquez et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0016285 A1 | 1/2007 | Lane et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0239265 A1 | 10/2007 | Birdsall |
| 2007/0244545 A1 | 10/2007 | Birdsall et al. |
| 2007/0244552 A1 | 10/2007 | Salahieh et al. |
| 2007/0270944 A1 | 11/2007 | Bergheim et al. |
| 2007/0288087 A1 | 12/2007 | Fearnot et al. |
| 2008/0021546 A1 | 1/2008 | Patz et al. |
| 2008/0021552 A1 | 1/2008 | Gabbay |
| 2008/0039934 A1 | 2/2008 | Styrc |
| 2008/0071361 A1 | 3/2008 | Tuval et al. |
| 2008/0071369 A1 | 3/2008 | Tuval et al. |
| 2008/0077236 A1 | 3/2008 | Letac et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0208327 A1 | 8/2008 | Rowe |
| 2008/0243245 A1 | 10/2008 | Thambar et al. |
| 2008/0243246 A1 | 10/2008 | Ryan et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0192599 A1 | 7/2009 | Lane et al. |
| 2009/0264997 A1 | 10/2009 | Salahieh et al. |
| 2009/0276027 A1 | 11/2009 | Glynn |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0100176 A1 | 4/2010 | Elizondo et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0262231 A1 | 10/2010 | Tuval et al. |
| 2010/0286768 A1 | 11/2010 | Alkhatib |
| 2010/0298931 A1 | 11/2010 | Quadri et al. |
| 2011/0022157 A1 | 1/2011 | Essinger et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |

(56) References Cited

U.S. PATENT DOCUMENTS

| | | |
|---|---|---|
| 2011/0282439 A1 | 11/2011 | Thill et al. |
| 2011/0301692 A1 | 12/2011 | Seguin |
| 2011/0319988 A1 | 12/2011 | Schankereli et al. |
| 2012/0035719 A1 | 2/2012 | Forster et al. |
| 2012/0035722 A1 | 2/2012 | Tuval |
| 2012/0046742 A1 | 2/2012 | Tuval et al. |
| 2012/0078347 A1 | 3/2012 | Braido et al. |
| 2012/0078357 A1 | 3/2012 | Conklin |
| 2012/0083878 A1 | 4/2012 | Sequin et al. |
| 2012/0101572 A1 | 4/2012 | Kovalsky et al. |
| 2012/0123529 A1 | 5/2012 | Levi et al. |
| 2012/0179244 A1 | 7/2012 | Schankereli et al. |
| 2012/0215303 A1 | 8/2012 | Quadri et al. |
| 2012/0232646 A1 | 9/2012 | Agathos |
| 2012/0277856 A1 | 11/2012 | Spenser et al. |
| 2012/0296418 A1 | 11/2012 | Bonyuet et al. |
| 2012/0303116 A1 | 11/2012 | Gorman, III et al. |
| 2012/0316642 A1 | 12/2012 | Yu et al. |
| 2013/0018458 A1 | 1/2013 | Yohanan et al. |
| 2013/0023984 A1 | 1/2013 | Conklin |
| 2013/0150956 A1 | 6/2013 | Yohanan et al. |
| 2013/0204359 A1 | 8/2013 | Thubrikar et al. |
| 2013/0211508 A1 | 8/2013 | Lane et al. |
| 2013/0218267 A1 | 8/2013 | Braido et al. |
| 2013/0274870 A1 | 10/2013 | Lombardi et al. |
| 2013/0274873 A1 | 10/2013 | Delaloye et al. |
| 2013/0338765 A1 | 12/2013 | Braido et al. |
| 2014/0121763 A1 | 5/2014 | Duffy et al. |
| 2014/0142694 A1 | 5/2014 | Tabor et al. |
| 2014/0155997 A1 | 6/2014 | Braido |
| 2014/0194981 A1 | 7/2014 | Menk et al. |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350663 A1 | 11/2014 | Braido et al. |
| 2014/0350665 A1 | 11/2014 | Braido et al. |
| 2014/0350667 A1 | 11/2014 | Braido et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 19532846 | 3/1997 |
| DE | 19546692 A1 | 6/1997 |
| DE | 19857887 A1 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| DE | 10121210 A1 | 11/2002 |
| DE | 202008009610 U1 | 12/2008 |
| EP | 0103546 | 3/1984 |
| EP | 0144167 | 6/1985 |
| EP | 0592410 | 4/1994 |
| EP | 0515324 B1 | 12/1996 |
| EP | 0850607 A1 | 7/1998 |
| EP | 0597967 B1 | 12/1999 |
| EP | 1000590 A1 | 5/2000 |
| EP | 1057460 A1 | 12/2000 |
| EP | 1088529 | 4/2001 |
| EP | 1360942 A1 | 11/2003 |
| EP | 1570809 A1 | 9/2005 |
| EP | 1584306 A1 | 10/2005 |
| EP | 1598031 A2 | 11/2005 |
| EP | 1926455 A2 | 6/2008 |
| EP | 2047824 A1 | 4/2009 |
| EP | 2059192 B1 | 5/2009 |
| EP | 2254513 A1 | 12/2010 |
| EP | 2537487 A1 | 12/2012 |
| EP | 2620125 A1 | 7/2013 |
| EP | 2749254 A1 | 7/2014 |
| EP | 2815725 A1 | 12/2014 |
| FR | 2788217 A1 | 7/2000 |
| FR | 2847800 A1 | 6/2004 |
| FR | 2850008 A1 | 7/2004 |
| GB | 1477643 A | 6/1977 |
| GB | 2056023 | 3/1981 |
| JP | 2008541865 A | 11/2008 |
| JP | 2011500241 A | 1/2011 |
| JP | 2011522634 A | 8/2011 |
| JP | 2011528256 A | 11/2011 |
| JP | 2012504031 A | 2/2012 |
| SU | 158988 | 11/1963 |
| SU | 1271508 | 11/1986 |
| SU | 1371700 | 2/1988 |
| SU | 1457921 A1 | 2/1989 |
| WO | 9117720 A1 | 11/1991 |
| WO | 9217118 | 10/1992 |
| WO | 9301768 B1 | 2/1993 |
| WO | 9716133 A1 | 5/1997 |
| WO | 9724080 A1 | 7/1997 |
| WO | 9832412 A2 | 7/1998 |
| WO | 199829057 A1 | 7/1998 |
| WO | 9913801 A1 | 3/1999 |
| WO | 9933414 | 7/1999 |
| WO | 9940964 | 8/1999 |
| WO | 9947075 | 9/1999 |
| WO | 0018333 A1 | 4/2000 |
| WO | 200041652 A1 | 7/2000 |
| WO | 200047139 A1 | 8/2000 |
| WO | 01028459 A1 | 4/2001 |
| WO | 0135878 A2 | 5/2001 |
| WO | 0149213 A2 | 7/2001 |
| WO | 200149213 A2 | 7/2001 |
| WO | 0154624 A1 | 8/2001 |
| WO | 01054625 A1 | 8/2001 |
| WO | 01056500 A2 | 8/2001 |
| WO | 200162189 A1 | 8/2001 |
| WO | 2001054625 A1 | 8/2001 |
| WO | 0164137 | 9/2001 |
| WO | 0166035 A2 | 9/2001 |
| WO | 0166037 A2 | 9/2001 |
| WO | 01076510 A2 | 10/2001 |
| WO | 0222054 | 3/2002 |
| WO | 0236048 A1 | 5/2002 |
| WO | 0241789 | 5/2002 |
| WO | 02036048 A1 | 5/2002 |
| WO | 0243620 | 6/2002 |
| WO | 0247575 A2 | 6/2002 |
| WO | 0249540 | 6/2002 |
| WO | 03037222 A2 | 5/2003 |
| WO | 03047468 A1 | 6/2003 |
| WO | 2003047468 A1 | 6/2003 |
| WO | 03075799 A1 | 9/2003 |
| WO | 2004016200 A2 | 2/2004 |
| WO | 2005062980 A2 | 7/2005 |
| WO | 2005087140 A1 | 9/2005 |
| WO | 2006014233 A2 | 2/2006 |
| WO | 2006034008 A2 | 3/2006 |
| WO | 06073626 A2 | 7/2006 |
| WO | 2006124649 A2 | 11/2006 |
| WO | 2006127765 A1 | 11/2006 |
| WO | 2006128193 A2 | 11/2006 |
| WO | 2007053243 A2 | 5/2007 |
| WO | 2007071436 A2 | 6/2007 |
| WO | 2008005405 A2 | 1/2008 |
| WO | 2008035337 A2 | 3/2008 |
| WO | 08070797 A2 | 6/2008 |
| WO | 2008100600 A1 | 8/2008 |
| WO | 2008147964 A1 | 12/2008 |
| WO | 2008150529 A1 | 12/2008 |
| WO | 2009024859 A2 | 2/2009 |
| WO | 2009042196 A2 | 4/2009 |
| WO | 2009045338 A1 | 4/2009 |
| WO | 2009053497 A1 | 4/2009 |
| WO | 2009061389 A2 | 5/2009 |
| WO | 2009149462 A2 | 12/2009 |
| WO | 10008548 A2 | 1/2010 |
| WO | 10008549 A1 | 1/2010 |
| WO | 2010037141 A1 | 4/2010 |
| WO | 10096176 A1 | 8/2010 |

(56) References Cited

FOREIGN PATENT DOCUMENTS

| WO | 10098857 A1 | 9/2010 |
|---|---|---|
| WO | 2010141847 A1 | 12/2010 |
| WO | 2011057087 A1 | 5/2011 |
| WO | 2012032187 A1 | 3/2012 |
| WO | 2012161786 A1 | 11/2012 |

OTHER PUBLICATIONS

Extended European Search Report for Application No. 14180625.7 dated Nov. 24, 2014.
Extended European Search Report for Application No. 14180623.2 dated Nov. 24, 2014.
Al Zaibag, Muayed, et al., "Percutaneous Balloon Valvotomy in Tricuspid Stenosis," British Heart Journal, Jan. 1987,vol. 57, No. 1, pp. 51-53.
Al-Khaja, N., et al., "Eleven Years' Experience with Carpentier-Edwards Biological Valves in Relation to Survival and Complications," European Journal of Cardiothoracic Surgery 3:305-311, Jun. 30, 2009.
Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Bullesfeld et al., Percutaneous Implantation of the First Repositionable Aortic Valve Prosthesis in a Patient With Severe Aortic Stenosis, Catheterization & Cardiovascular Interventions 71:579-84 (2008).
Curriculum Vitae of Robert A. Ersek, M.D., FACS, Jul. 10, 2009, http://www.ersek.com/rae-cv.htm.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Evidence—Anlage 3 (Photograph).
Grube et al., "Percutaneous Implantation of the CoreValve Self-Expanding Valve Prosthesis in High-Risk Patients With Aortic Valve Disease" (2006).
Inoune, M.D., Kanji, et al., "Clinical Application of Transvenous Mitral Commissurotomy by a New Balloon Catheter," The Journal of Thoracic and Cardiovascular Surgery 87:394-402, 1984.
International Search Report and Written Opinion PCT/US2014/ 020872 dated Mar. 19, 2014.
International Search Report from corresponding PCT application No. PCT/US2011/054973 dated Apr. 23, 2012.
Kolata, Gina, "Device That Opens Clogged Arteries Gets a Failing Grade in a New Study," nytimes.com, http://www.nytimes.com/ 1991/01/03/health/device-that-opens-clogged-arteri- es-gets-a-faili . . . , Jul. 29, 2009, 2 pages.
Lawrence, Jr., M.D., David D., "Percutaneous Endovascular Graft: Experimental Evaluation," Radiology 1897; 163: 357-360.
Merriam Webster definition of "prevent," www.merriam-webster.com/dictionary/prevent.
Merriam Webster definition of "retard," www.merriam-webster.com/dictionary/retard.
Moazami et al., "Transluminal Aortic Valve Placement" (1996).
Moazami et al., "Transluminal Aortic Valve Placement, A Feasibility Study With a Newly Collapsible Aortic Valve," (1996).
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, pp. 199-203, English translation of Abstract only.
Rashkind, M.D., William J., "Creationof an Atrial Septal Defect Withoput Thoracotomy," the Journal of the American Medical Association, vol. 196, No. 11, Jun. 13, 1966, pp. 173-174.
Rashkind, M.D., William J., "Historical Aspects of Interventional Cardiology: Past, Present, Future," Texas Heart Institute Journal, Interventional Cardiology, pp. 363-367.
Rosch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional cardiology, 2nd Edition, W.B. Saunders Company, Philadelphia, PA, .COPYRGT. 1994, 1990, pp. 803-815.
U.S. Appl. No. 13/572,842, filed Aug. 13, 2012, Kovalsky.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Medecine et Hygiene, Geneve, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.
Excerpt from Transcatheter Aortica Valve Implantation—Tips and Tricks to Avoid Failure, Patrick Serruys et al., published 2010 by Informa Healthcare, UK.
Andersen, H. R. et al, Transluminal implantation of artificial heart valves, European Heart Journal (1992) 13, 704-708.
Andersen, Henning Rud, Transluminal Catheter Implanted Prosthetic Heart Valves, International Journal of Angiology (1998) 7:102-106.
International Search Report PCT/US2009/004094 dated Mar. 3, 2010.
Knudsen, L.L. et al., Catheter-implanted prosthetic heart valves, The International Journal of Artificial Organs, vol. 16, No. 5 1993, pp. 253-262.
Moazami, Nader et al., Transluminal Aortic Valve Placement, ASAIO Journal, 1996; 42:M381-M385.
Quaden, Renè et al., "Percutaneous aortic valve replacement: resection before implantation," 836-840, European J. of Cardio-thoracic Surgery 27 (2005).
Ruiz, Carlos, Overview of PRE-CE Mark Transcatheter Aortic Valve Technologies, Euro PCR (powerpoint—dated May 25, 2010).
U.S. Appl. No. 29/375,243, filed Sep. 20, 2010.
U.S. Appl. No. 29/375,260, filed Sep. 20, 2010.
Zegdi, Rachid, MD, PhD et al., "Is it Reasonable to Treat All Calcified Stenotic Aortic Valves With a Valved Stent?" 579-584, J. of the American College of Cardiology, vol. 51, No. 5, Feb. 5, 2008.
78. Heart repairs without surgery. Minimally invasive procedures aim to correct valve leakage. PubMed ID 15586429, Heart Advisor, Sep. 2004.
Buellesfeld et al., Treatment of paravalvular leaks through inverventional techniques; Department of Cardiology, Ben University Hospital 2011.
De Cicco, Giuseppe, et al. "Aortic valve periprosthetic leakage: anatomic observations and surgical results." The Annals of thoracic surgery 79.5 (2005): 1480-1485.

(56) References Cited

OTHER PUBLICATIONS

European Communication for Application No. 09788918.2 dated Jun. 29, 2015.

Gössl, Mario, and Charanjit S. Rihal. "Percutaneous treatment of aortic and mitral valve paravalvular regurgitation." Current cardiology reports 15.8 (2013): 1-8.

Hourihan, Maribeth et al., Transcatheter Umbrella Closure of Valvular and Paravalvular Leaks, Hourihan et al., Journal of the American College of Cardiology, vol. 20, No. 6, pp. 1371-1377, (1992).

Muñoz, Daniel Rodriguez, Carla Làzaro Rivera, and Josè Luis Zamorano Gómez. "Guidance of treatment of perivalvular prosthetic leaks." Current cardiology reports 16.1 (2014): 1-6.

Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.

Swiatkiewicz, Iwona, et al. "Percutaneous closure of mitrel perivalvular leak." Kardiologia polska 67.7 (2009): 762.

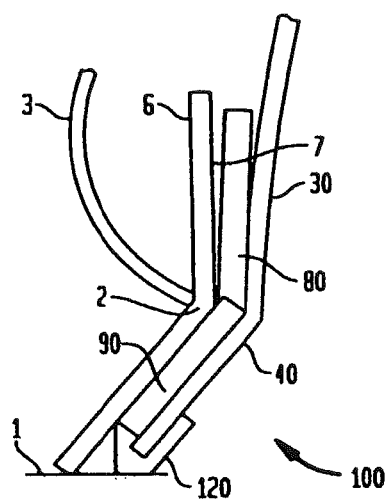
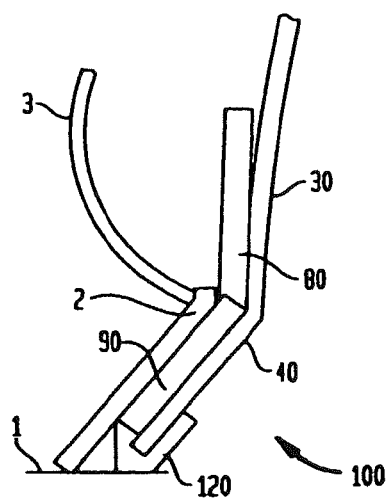

COLLAPSIBLE AND RE-EXPANDABLE PROSTHETIC HEART VALVE CUFF DESIGNS AND COMPLEMENTARY TECHNOLOGICAL APPLICATIONS

CROSS-REFERENCE TO RELATED APPLICATIONS

This application is a divisional application of U.S. application Ser. No. 12/737,256 filed Dec. 22, 2010, which is a national phase entry under 35 U.S.C. § 371 of International Application No. PCT/US2009/004094 filed Jul. 15, 2009, published in English, which claims the benefit of the filing date of U.S. Provisional Patent Application No. 61/134,995 filed Jul. 15, 2008, the disclosures of all of which are hereby incorporated herein by reference.

FIELD OF THE INVENTION

The present invention is directed to prosthetic heart valves for replacement of native heart valves, to components for use in such prosthetic heart valves, and to methods of treating patients with such prosthetic heart valves.

BACKGROUND OF THE INVENTION

Certain prosthetic heart valves incorporate an expandable stent body and valve elements such as prosthetic valve leaflets mounted to the stent body. The prosthetic valve may also include a cuff including one or more layers of materials such as fabric or animal tissue. Valves of this type may be implanted in the heart by advancing the valve into the body of the patient with the stent body and cuff in a collapsed condition in which the stent body and cuff have a relatively small diameter. Once the valve is positioned at the desired implantation site, the stent body is brought to an expanded condition in which a portion of the stent body has a generally tubular shape. This portion engages the surrounding native tissue and holds the valve in place. The cuff forms a lining covering all or part of the tubular stent body. The valve acts as a functional replacement for the diseased native valve. Thus, the valve elements inside the stent body permit blood flow in the antegrade direction but substantially block flow in the opposite, retrograde direction. For example, a prosthetic valve may be advanced to a site within a diseased native aortic valve percutaneously through the arterial system and into the aorta to the native aortic valve. In a transapical placement, a prosthetic valve may be advanced through an incision in the apex of the heart and through the left ventricle to the native aortic valve. Other approaches through other access sites can be used. Once the prosthetic valve is in place, it permits flow from the left ventricle into the aorta when the left ventricle contracts during systole, but substantially blocks retrograde flow from the aorta into the left ventricle during diastole.

There are significant challenges in design of an expandable valve. For example, the valve desirably can be collapsed to a relatively small diameter to facilitate advancement into the body. This imposes significant limitations on the design of the cuff as, for example, the thickness of the material which can be incorporated in the cuff. However, the stent body must be capable of expanding to an operative, expanded condition in which the stent body securely engages the surrounding native tissues to hold the valve in place. The stent body and the cuff carried on the stent body should form a good seal with the surrounding native tissues to prevent leakage around the outside of the prosthetic valve, commonly referred to as perivalvular leakage. However, the stent body and cuff should not apply excessive forces to the annulus of the native valve. Excessive forces on the annulus of the native aortic valve can disrupt the electrical conduction system of the heart and also can impair the functioning of the mitral valve. These issues are complicated by the fact that the diseased native valve leaflets and other diseased tissues may present an implantation site which is irregular. For example, patients with calcified or stenotic aortic valves may not be treated well with the current collapsible valve designs, and may encounter problems such as (1) perivalvular leakage (PV leak), (2) valve migration, (3) mitral valve impingement, (4) conduction system disruption, etc., all of which can lead to adverse clinical outcomes. To reduce these adverse events, the optimal valve would seal and anchor adequately without the need for excessive radial force that could harm nearby anatomy and physiology.

Numerous prosthetic valve and stent body designs have been proposed. However, despite all of the attention devoted to such designs, still further improvements would be desirable.

BRIEF SUMMARY OF THE INVENTION

One aspect of the present invention provides a prosthetic heart valve. The valve according to this aspect of the invention desirably includes a stent body having a generally tubular annulus region. The stent body, and particularly the annulus region, has a proximal-to-distal axis. The stent body has a radially collapsed condition and a radially expanded condition, the annulus region increasing in diameter during transition from the radially collapsed condition to the radially expanded condition. The valve according to this aspect of the invention desirably includes one or more prosthetic valve elements as, for example, prosthetic valve leaflets. The prosthetic valve elements are mounted to the stent body and are operative to allow flow in the antegrade direction through the annulus region but to substantially block flow in the retrograde direction through the annulus region when the stent body is in the radially expanded condition.

The valve according to this aspect of the invention most preferably includes a cuff secured to the stent body. The cuff may include a first cuff portion covering at least a portion of the annulus region for disposition at said native valve annulus, the first cuff portion having a first diameter when the annulus region is in the radially expanded condition. In this aspect of the invention, the cuff desirably also includes a second cuff portion proximal to the first cuff portion, the second cuff portion having a second diameter when the annulus region is in the radially expanded condition, the second diameter being greater than the first diameter. The second cuff portion preferably is adapted for engagement with native tissue proximal to the native valve annulus. For example, where the prosthetic valve is implanted in a diseased native aortic valve, the second cuff portion may engage the left ventricular outflow tract or LVOT.

A further aspect of the invention provides a prosthetic valve which may have a stent body and valve element as discussed above. A valve according to this aspect of the invention desirably includes a cuff secured to the stent body and surrounding the annulus region, the cuff having one or more pleats adapted to collapse in axial directions and expand in radial directions upon transition of the stent body from the radially collapsed condition to the radially expanded condition. As further discussed below, the pleats can promote effective sealing with the surrounding native structures.

A valve according to yet another aspect of the invention desirably includes a stent body with a generally tubular annulus region having a proximal-to-distal axis, and desirably also includes prosthetic valve elements mounted to the stent body as discussed above. The valve according to this aspect of the invention most preferably has a cuff secured to the stent body and surrounding the annulus region; and also has one or more biasing elements separate from the cuff. The biasing elements are mechanically connected to the stent body and to the cuff, and are adapted to bias at least a portion of the cuff outwardly with respect to the stent body. Merely by way of example, the biasing elements may include springs formed separately from the stent body or integral with the stent body, and may also include a hygroscopic, water-swellable material disposed between the cuff and the stent body. By biasing the cuff outwardly from the stent body, the biasing elements tend to promote intimate engagement between the cuff and the surrounding tissues, even where the surrounding tissues are irregular.

A still further aspect of the invention provides a prosthetic valve which includes an expansible stent body and valve elements, and which also includes a cuff secured to the stent body. The cuff desirably has a mobile portion movable in an axial direction with respect to the stent body so that when the stent body is in the radially collapsed condition, the mobile portion of the cuff is axially offset from the annulus region of the stent body. Most preferably, the mobile portion of the cuff can be displaced to an operative position in which the mobile portion of the cuff extends around the annulus section. For example, the cuff may have a generally tubular wall with a fixed end attached to the stent body and a free end projecting axially away from the annulus section when the stent body is in the radially collapsed condition. In this arrangement, the mobile portion of the cuff includes the free end of the tubular wall. The tubular wall desirably is constructed and arranged so that the tubular wall may be turned inside-out so as to bring the free end of the tubular wall into the operative position. Thus, the free end of the tubular wall extends around the annulus region when the cuff is in the operative position.

Still another aspect of the invention provides a valve with a stent body and valve elements. The valve further includes a cuff having pockets with open sides. The open sides face in an axial direction, such as in the distal direction, so that flow of blood will tend to expand the pockets and bring the cuff into tighter engagement with the surrounding tissues.

Yet another aspect of the invention provides a valve having a stent body, valve elements, and a cuff having a plurality of regions arranged around the circumference of the stent body. In an operative, implanted condition, the regions of the cuff have differing radial thickness. For example, the cuff may include plural bulge regions separated from one another by intermediate regions having lesser radial thickness than the bulge regions. For example, a valve implanted in a generally triangular opening in a stenosed tricuspid arterial valve may have three bulge regions. The bulge regions may be lodged in the corners of the triangular opening. The various regions of the cuff may be provided with individual inflatable chambers, so that bulge regions and intermediate regions can be formed as required for an individual patient.

Still other aspects of the invention provide methods of implanting a valve such as those discussed above, and kits for performing such methods.

BRIEF DESCRIPTION OF THE DRAWINGS

The present invention may be more fully appreciated with reference to the following detailed description, which in turn refers to the drawings, wherein:

FIG. 5 is a fragmentary, diagrammatic sectional view depicting portions of the valve of FIGS. 3 and 4 in an implanted condition, in conjunction with portions of the native tissue;

FIG. 6 is a view similar to FIG. 5 depicting the valve of FIGS. 3 and 4 in a different implanted condition;

DETAILED DESCRIPTION

Figure 1:
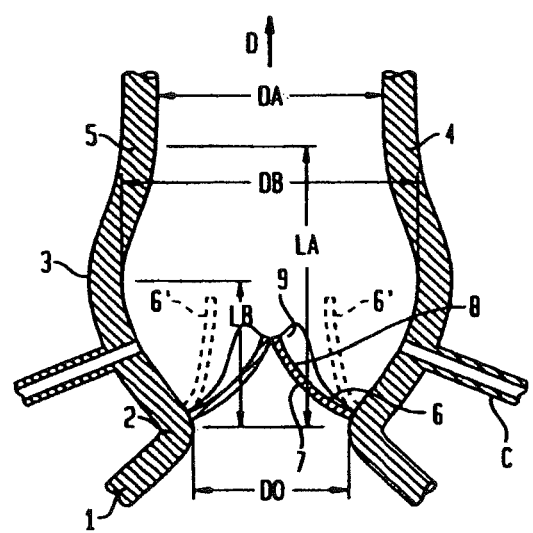
FIG. 1 is a schematic sectional representation of an aortic root anatomy.

FIG. 1 is a simplified view of the geometry or anatomy of the aortic root tissue in a typical human heart. The left ventricular outflow tract (LVOT) 1 communicates with the ascending aorta 5 through the annulus 2 of the native aortic valve and the Valsalva sinus 3. The sinus joins the aorta at the sinotubular junction (STJ) 4. The native aortic valve typically includes three native valve leaflets 6, of which only two are visible in FIG. 1. As the left ventricle contracts during systole, blood is forced from the LVOT 1 through the native valve and sinus and into the aorta 5, moving generally in the downstream or antegrade flow direction indicated by arrow D. Each native valve leaflet has an interior surface 7 facing generally proximally and generally inwardly, toward the other native valve leaflets, and has an opposite-facing exterior surface 8. In a healthy individual, the native valve leaflets 6 open away from one another and move to the position schematically shown in broken lines at 6' to permit flow in this direction. During diastole, when the ventricle is not contracting, the native valve leaflets 6 move back to the position indicated in solid lines in FIG. 1, where they abut one another or "coapt" so as to substantially block flow in the upstream or retrograde direction, opposite to arrow D. The direction "distal" as used herein with reference to a feature of the native circulatory system refers to the direction of antegrade flow, i.e., the predominant direction of blood flow through such feature, as indicated by arrow D. The direction "proximal" as used herein with reference to a feature of the native circulatory system is the opposite direction.

The parameters identified in FIG. 1 are as follows: DO=orifice diameter, i.e., the interior diameter of native annulus 2; DA=the diameter of the aorta just distal to the sinus; DB=maximum projected sinus diameter (this sinus is sometimes known as the Valsalva sinus); LA=length of the sinus, i.e., the dimension in the distal direction from the annulus 2 to the sinotubular junction 4; and LB=distance in the distal direction between DO and DB.

The leaflets 6 have distal edges 9 remote from the annulus 2. Each native leaflet 6 has a surface 7, referred to herein as the "interior" surface of the leaflet, facing generally towards the other leaflets. Each native leaflet 6 also has a surface 8, referred to herein as the "exterior" surface of the leaflet, facing outwardly, away from the other leaflets and toward the wall of the sinus 3. The cross sectional shape of such a native valve varies somewhat from individual to individual, and this variation can be increased by various types of disease. For example, disease can reshape the cross section of a patient's valve to a circular, triangular, or elliptical shape, depending on the disease state.

An expandable stent body 10 (FIG. 2) for a prosthetic heart valve in accordance with one embodiment of the present invention is formed as a unitary structure as, for example, by laser cutting or etching a tube of a super elastic metal alloy such as a nickel-titanium alloy of the type sold under the designation NITINOL. Such a unitary structure can also be referred to as a "non-woven" structure, in that it is not formed by weaving or winding one or more filaments. In the fully-expanded, unconstrained configuration depicted in FIG. 2, stent body 10 includes an annulus section 30, an aorta section 20 and support struts 60 extending between the annulus section and the aorta section. The annulus section 30 in the expanded configuration is generally in the form of a cylindrical tube having a central axis 14, whereas aorta section 20 is generally in the form of a hoop coaxial with the annulus section. In the expanded configuration, the annulus section is of substantially constant diameter except that the annulus section has a flared region 40 at one end. The tubular annulus section 30 has a wall formed by numerous cell struts interconnected to form a plurality of cells. The aorta section 20 is defined by a similar wall formed of multiple cells, each of which includes a plurality of interconnected cell struts.

The stent body is adapted for installation in the body of a patient with the annulus section adjacent the annulus 2 (FIG. 1) and with the aorta section 20 adjacent the sinotubular junction 4 and aorta 5. Thus, when the valve incorporating the stent body is placed in the patient, the aorta section 20 will be disposed distal to the annulus section 30 in the frame of reference of the patient's circulatory system. Accordingly, as used with reference to features of the stent body and valve, the direction D (FIG. 2) along axis 14 from the flared region 40 of the annulus section 30 through the annulus section and from the annulus section towards the aorta section 20 is referred to as the distal direction, and the opposite direction is taken as the proximal direction. Stated another way, the distal direction along the stent body is the direction from the end of the stent which is intended for disposition at a proximal location in the frame of reference of the circulatory system to the end of the stent which is intended for disposition at a more distal location in the frame of reference of the circulatory system. The "axial" directions as referred to herein are the proximal and distal directions. Also, the outward direction as used with reference to the valve is the direction away from the proximal-to-distal axis 14. As used with reference to features of the valve, the "circumferential" directions are the directions around axis 14.

Stent body 10 includes features which facilitate attachment of valve leaflets as discussed further below. In this particular stent body, the leaflet attachment features include three commissure posts 50 formed integrally with the remainder of the stent and extending axially in the annulus section 30. The commissure posts are connected to the cell struts of the annulus section and are spaced equidistantly around the annulus section 30.

Figure 2:
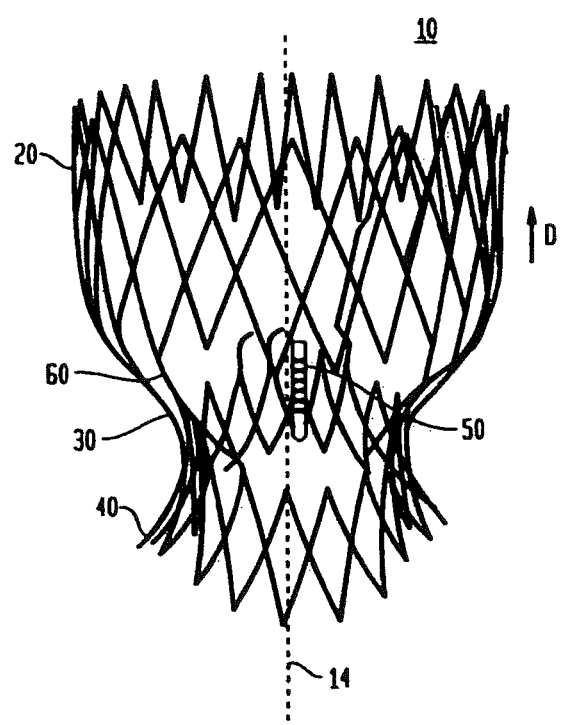
FIG. 2 is a perspective view of a portion of a stent body used in one embodiment of the present invention.
Figure 33:
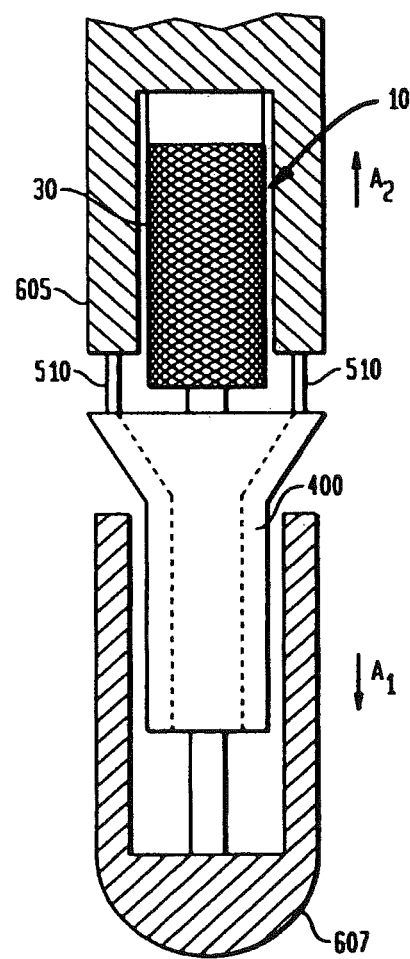
FIG. 33 is a fragmentary, diagrammatic sectional view depicting a valve according to yet another embodiment of the present invention.
Figure 34:
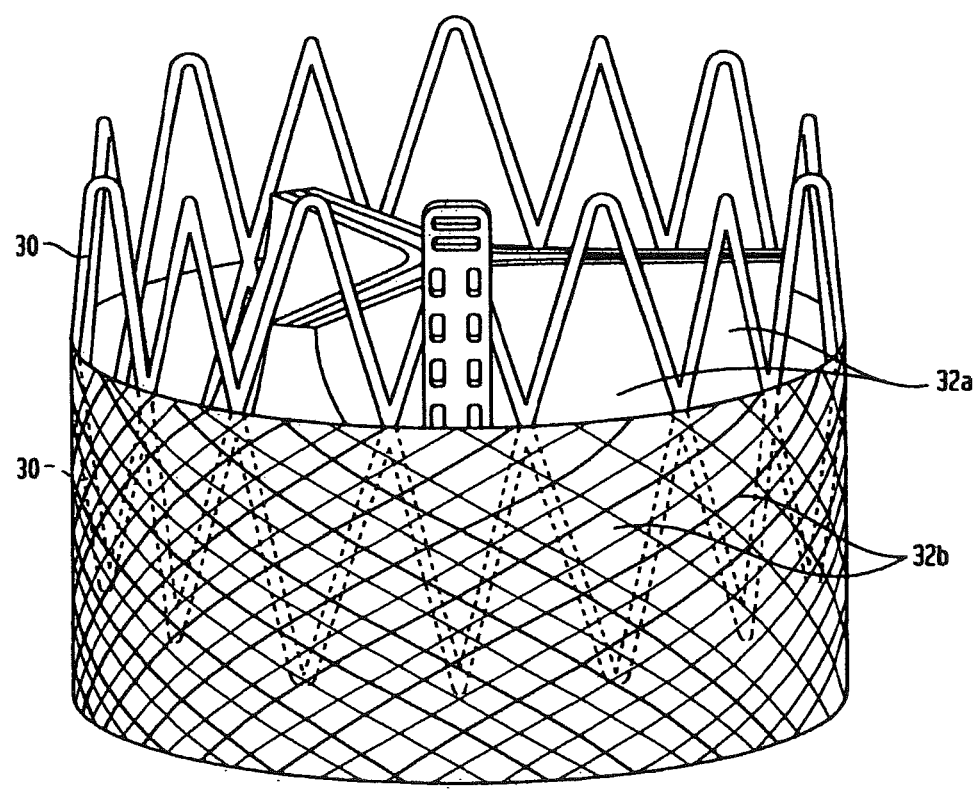
FIG. 34 is a partial, side, perspective view of a valve according to a further embodiment of the present invention.

The particular construction of stent body 10 that is shown in FIG. 2 (and subsequent figures) is only an example. Numerous other collapsible and expandable stent bodies can be used. Merely by way of example, the annulus region may include multiple rows of cells; leaflet attachment features other than the axially-extensive posts can be used; and the aorta section 20 and struts 60 may be omitted. As one example, FIG. 33 shows a stent variation with multiple rows of circumferentially collapsible/expandable cells in the annular valve section 30 of the stent body 10. Referring to FIG. 34, a few representative cells in the more distal or downstream row are numbered 32a, while a few representative cells in the more proximal or upstream row are numbered 32b. The locations of some of the cells that are otherwise obscured by cuff material in FIG. 34 are enhanced by the addition of dotted lines.

Figure 3:
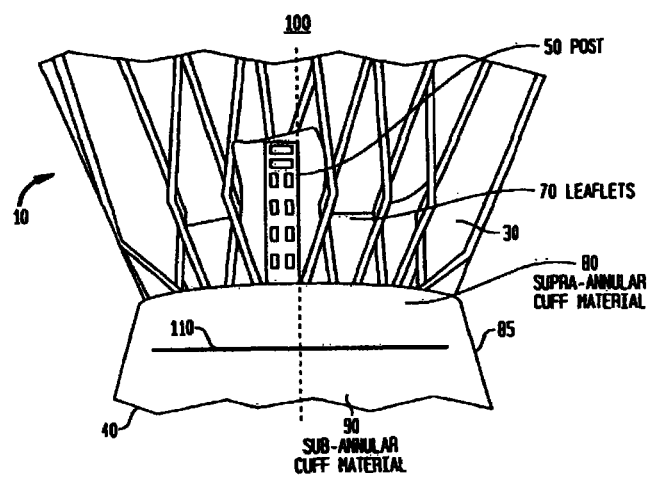
FIG. 3 is a partial elevational view of a valve in accordance with one embodiment of the present invention.

A valve 100 (FIG. 3) incorporating a stent body 10 similar to that discussed above with reference to FIG. 2 includes three flexible prosthetic leaflets 70 formed from a biocompatible material such as an animal tissue as, for example, pericardial tissue or a synthetic polymeric material such as a silicone-polyurethane polymer. The leaflets are mounted to the stent body as, for example, by suturing the leaflets to posts 50, so that when the valve and stent body are in an expanded condition as depicted in FIG. 3, the leaflets are disposed in whole or in part within the annulus section 30 of the stent body.

Figure 4:
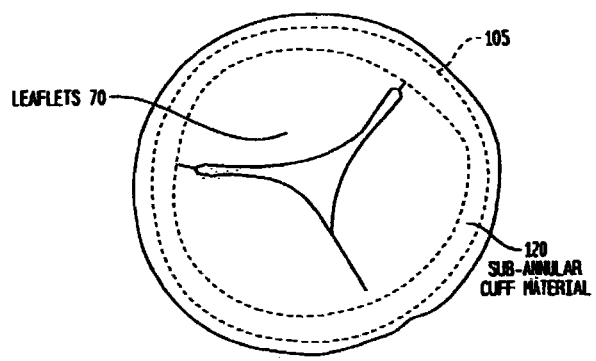
FIG. 4 is an end view of the valve depicted in FIG. 3.

The valve also includes a cuff 85. The cuff includes a first cuff portion 80, also referred to herein as a supra-annular cuff portion, extending over a region of the tubular wall of the annulus section 30 remote from the proximal end of the annulus section and distal to the flared region 40 of the annulus section. The cuff also includes a second portion, also referred to herein as the sub-annular cuff portion 90, proximal to the first portion 80. A line 110 is shown in FIG. 3 as a boundary between these two cuff portions for clarity of illustration. In actual practice, there may or may not be a visible demarcation between these portions. Line 110 is approximately at the bottom of commissure posts 50. Stated another way, in this embodiment, the second cuff portion 90 is disposed proximal to the commissure posts and proximal to the prosthetic leaflets 70. In the embodiment shown in FIG. 3, both first cuff portion 80 and the second cuff portion 90 extend over the exterior surface of the stent body, i.e., the surface facing outwardly away from axis 14. The second or sub-annular cuff portion 90 also includes a layer of material 120 (FIG. 4) on the interior surface of the flared portion 40 of the stent. Thus, the second or sub-annular portion 90 of the cuff is thicker than the first or supra-annular portion 80. A broken line 105 is shown in FIG. 4 for clarity of illustration at the juncture of inner layer 120 and the layer on the exterior surface, i.e., at the proximal edge of the stent body. In actual practice there may be no visible boundary at this location. In the particular embodiment depicted in FIG. 4, the entire cuff 85 is formed from a unitary sheet of material. Layer 120 is integral with the cuff material on the exterior of the stent, and is formed by folding the unitary sheet around the proximal edge of the stent. The material on the interior and exterior of the stent may be sutured together.

This particular embodiment is only illustrative; in other arrangements, the cuff portions 80 and 90 may be formed as separate pieces of the same or different materials. Either or both cuff portions may include one or more layers on the inside of the stent body, one or more layers on the outside of the stent body, or both. The layers on the inside and outside of the cuff may be formed separately from one another or integrally with one another. The cuff desirably is attached to the stent as, for example, by suturing to the cell struts, to the junctures between the cell struts, or both. The cuff may be formed from materials such as animal tissues as, for example, porcine, ovine and bovine pericardium, porcine sub-mucosa, and synthetic fabrics such as knit or woven polyester, and non-woven fabrics. Collagen-impregnated fabrics may be used. Also, bio-absorbable materials such as polyglactin, copolymers of lactide and caprolactone, and polylactides can be used.

FIG. 4 shows valve 100 (FIG. 3) as seen in axial view, looking distally from the proximal end of the valve. The three flexible leaflets 70 can be seen in FIG. 4 in their nearly closed condition (i.e., upper "free" edges of the leaflets coming together in approximately a Y pattern). The valve is preferably designed to close with fully redundant coaptation when under diastolic back-pressure.

In operation, the valve is brought to a collapsed condition and mounted on a delivery device (not shown) such as an elongated probe having a sheath adapted to retain the stent body in the collapsed condition. The delivery device may include a mechanical or other arrangement for releasing the stent body from the sheath once the valve has been advanced to the desired location within the body. For example, the delivery device may be arranged to move the sheath with respect to the stent body in response to a manipulation by the operator. In the collapsed condition, the stent body, including the annulus section 30 and aorta section 20, is radially compressed. The prosthetic valve leaflets 70 are folded within the stent body. Because the thick second or sub-annular portion 90 of the cuff is disposed proximal to the valve leaflets, it does not impede collapse of the valve to a relatively small diameter.

The delivery device is advanced into the patient's body until the valve is aligned with the native aortic valve, with the annulus section 30 adjacent the annulus of the aorta. The valve is released from the sheath and stent body 10 expands under its own resilience. The resilient expansion may occur solely as a result of release of mechanical constraint of the stent body, or may include expansion resulting from the effects of temperature change on the material of the stent body. In this embodiment, the entire expansion of the stent body from its collapsed condition to its expanded, operative condition is brought about by the stent body itself. Stated another way, the stent body desirably is fully self-expanding and does not require a balloon or mechanical movement device to bring about any part of the expansion. As best seen in FIG. 5, the annulus section 30 brings the supra-annular or first section 80 of the cuff into engagement with the annulus 2 of the native aortic valve, and into engagement with the interior surfaces 7 of the native valve leaflets. Expansion of the annulus section 30, and particularly expansion of the flared portion 40, brings the second or sub-annular section 90 of the cuff into engagement with the LVOT proximal to the annulus 2. The cuff forms a seal with the native anatomy. Depending on the anatomy of the particular patient, the seal may be formed with one or more of the interior surfaces 7 of the native valve leaflets, the annulus and the LVOT. The aorta section 20 (FIG. 1) engages the native anatomy at or near the sinotubular junction 4.

Although the stent reaches an expanded configuration, it typically does not reach its fully-expanded, unconstrained configuration. Thus, the resilience of the stent body typically causes the aortic section 20 to bear on the sinotubular junction and also causes the annulus section 30 to bear on the annulus and on the interior surfaces of the leaflets, which helps to maintain the sealing engagement of the cuff with the native anatomy. The prosthetic valve leaflets 70 open to allow distal or antegrade flow of blood during systole, and close to block proximal or retrograde flow during diastole. The sealing engagement of the cuff with the native anatomy helps to block retrograde flow around the outside of the stent body, commonly referred to as perivalvular leakage. The valve does not block flow to the coronary arteries. For example, the support struts 60 may extend across the Valsalva sinus, so that blood can flow to the coronary arteries through spaces between the support struts.

FIG. 6 is similar to FIG. 5, but shows the valve used in an alternative implantation procedure. In this procedure, the patient's native aortic valve leaflets have been resected (removed), typically prior to implanting prosthetic valve 100 in the patient as shown. In this embodiment as well, the first or supra-annular portion 80 of the cuff is engaged with the native valve annulus 2, whereas the second cuff portion 90 is in contact with the native anatomy proximal to annulus 2, i.e., with the distal end of the left ventricular outflow tract (LVOT).

The embodiment discussed above can be varied in many ways. For example, FIGS. 5 and 6 depict the cuff disposed only on the outside of the annulus region 30 and flare portion 40 of the stent body. However, the cuff may be disposed only on the inside or on both the inside and outside. Also, the stent body may not be entirely or even partially self-expanding. The stent body may be brought from its collapsed condition to an expanded, operative condition by one or more inflatable balloons or mechanical elements incorporated in the delivery device.

A valve according to a further embodiment includes a cuff 200 (FIG. 7) formed to extend around the exterior of the annulus section 202 of the stent. In the radially expanded condition of the stent body, the material of the cuff is pleated. In this embodiment as well, the stent is a radially collapsible structure, and may be similar to the stent body discussed above. For example, the annulus section may include numerous cells which cooperatively define a tubular wall, each such cell being formed from interconnected cell struts 204. In the radially collapsed condition (not shown), the cell struts are oriented more nearly parallel to the proximal-to-distal axis 214 of the stent body. Thus, as the stent is transformed from the radially expanded condition depicted in FIG. 7 to the radially collapsed condition, the annulus section tends to elongate in the axial direction. In the reverse transition, from the radially collapsed condition to the radially expanded condition, the annulus region decreases in axial length as it increases in diameter. The pleats in the cuff define a plurality of valley regions 203 and ridge regions 205 extending generally in the circumferential direction. As the stent decreases in axial length during transition to the radially expanded condition, the adjacent valley regions move toward one another. This facilitates radial expansion of the ridge regions. Optionally, the cuff may be attached to the stent body only in the valley regions. The pleats may or may not be present in the radially collapsed condition of the stent body. Stated another way, the axial extension of the stent body during radial collapse may collapse ridge regions 205 inwardly to the same diameter as the valley regions 203. In the radially expanded condition of the stent body, the pleats help to form an effective seal with the native tissue. Pleated cuffs according to this embodiment may be formed from the cuff materials discussed above. The pleats need not be exactly circumferential. For example, there may be one or more helical valley regions and one or more helical ridge regions, so that the valley and ridge regions cooperatively define a form generally like a screw thread.

Figure 7:
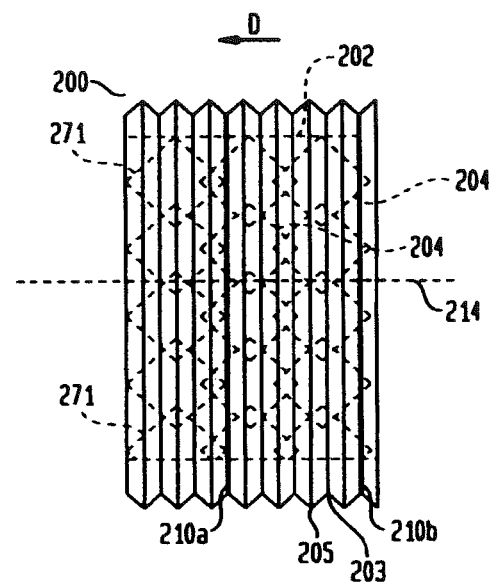
FIG. 7 is a fragmentary, a diagrammatic elevational view of a portion a valve according to a further embodiment of the invention.

The valve of FIG. 7 also includes biasing elements in the form of bands 210 of hygroscopic, sponge-like material that collapses easily and fills to a larger volume when the stent is expanded after implantation. Merely by way of example, the hygroscopic material may be a collagen foam or sponge similar to the material commercially available under the trademark Angioseal which is used to plug arteries, and to the similar material currently used for embolic protection. The biasing elements or bands 210 are formed separately from the cuff and are engaged between the ridge regions 205 of the cuff and the exterior surface of the annulus portion 202 of the stent. Thus, the biasing elements are mechanically engaged with the cuff and stent body. When the valve is implanted and the material of bands 210 swells, the biasing elements urge the ridge regions of the cuff outwardly with respect to the annulus region 202 of the stent body. In the embodiment of FIG. 7, the bands of hygroscopic material are disposed proximal to the prosthetic valve leaflets 271, and hence are axially offset from the leaflets. This facilitates collapse of the valve to a small diameter. In a valve according to yet another embodiment (FIG. 8), the biasing element includes a helical band 211 of hygroscopic material disposed inside the cuff 201.

Figure 8:
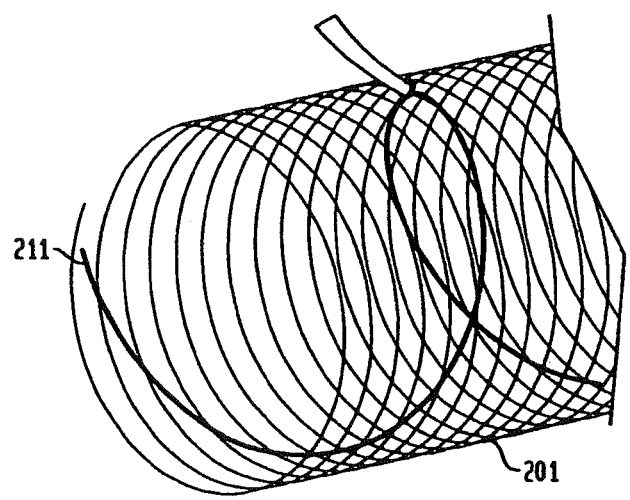
FIG. 8 is a fragmentary, diagrammatic perspective view depicting portions of a valve in accordance with yet another embodiment of the present the invention.

Biasing elements such as hygroscopic material can be used with cuffs other than the pleated cuffs shown in FIGS. 7 and 8. Bands of hygroscopic material can be integrated into the valve to take advantage of specific geometry in order to increase the sealing ability thereof, while not compromising (i.e., unduly increasing) the collapsed valve diameter. For example, in a valve which includes a cuff having a sub-annular portion as discussed above with reference to FIGS. 3 and 4, the biasing element can be located to expand the sub-annular cuff portion (i.e., on the upstream side of the patient's native valve annulus). Here again, because the biasing element is axially offset from the prosthetic valve elements, it does not add to the cross section of the prosthetic valve where the leaflets are when the valve is collapsed. In the collapsed condition, the bulk of the biasing element is not superimposed on the bulk of the leaflets. This helps make it possible to collapse the valve to a smaller circumferential size than would be possible if both the leaflets and biasing element were in the same cross sectional area of the valve.

In a further variant, a biasing element such as a water-absorbing polymer may be placed between layers of cuff material, so that the biasing element will urge the outer layer away from the stent body. In a further embodiment, the cuff material may be impregnated with such a polymer. When allowed to expand as a result of implantation in a patient and consequent absorption of water from the patient's tissue and/or blood, these materials can fill any gaps in the cuff material and can also fill gaps between the cuff material and the native tissue to reduce PV leakage.

Figure 9:
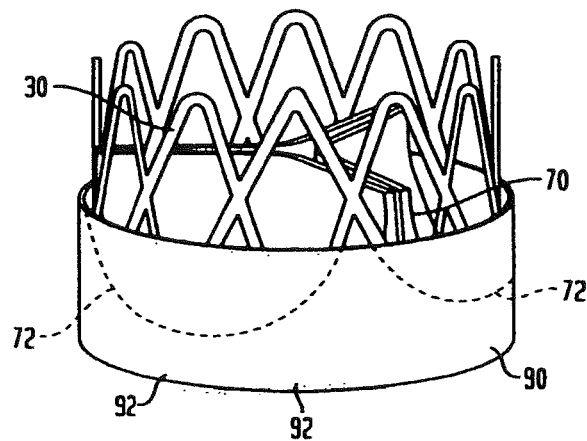
FIG. 9 is a diagrammatic perspective view of a valve according to another embodiment of the invention.

Staples and/or sutures can be used to secure the valve to the patient's native valve annulus using elongated instruments introduced trans-apically or percutaneously. The valve depicted in FIG. 9 has a stent body which has an annulus section 30 similar to the annulus section of the valve discussed above with reference to FIGS. 2-4. This particular valve body does not have an aortic section as used in the valve body of FIGS. 2-4. The annulus section 30 has a flared portion (not shown) at its proximal end, i.e., at the bottom of the drawing as seen in FIG. 9. In this embodiment as well, the cuff includes a second or sub-annular cuff portion 90. Cuff portion 90 can be sutured or stapled to the patient's native tissue because the bases or proximal edges of the prosthetic valve leaflets 70 are downstream from cuff portion 90. Dotted lines 72 in FIG. 9 indicate the approximate locations of the leaflet bases. Areas 92 of the second cuff portion 90 are thus available for stapling or suturing through cuff 90 into the patient's native tissue without interfering with prosthetic leaflets 70.

Figure 10:
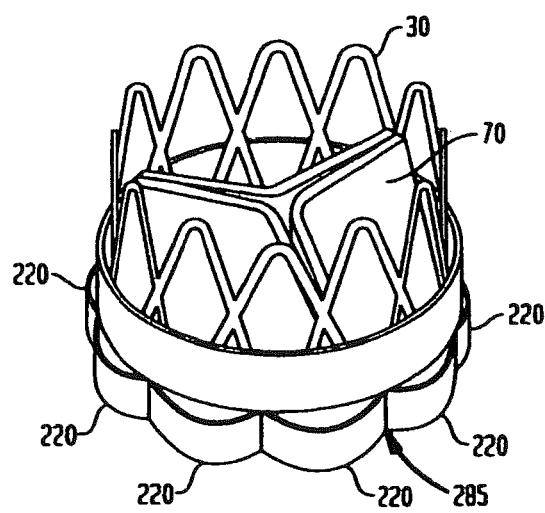
FIG. 10 is a diagrammatic perspective view of a valve according to a further embodiment of the invention.

The valve of FIG. 10 includes a cuff 285 defining multiple pockets 220. Each cuff has an open side facing in the distal direction. The other sides of each cuff are substantially closed. When the valve is implanted, these pockets will impede perivalvular leakage or retrograde blood flow around the outside of the stent body. Retrograde flow will tend to fill each pocket with blood and thus bias the outer surface of the pocket outwardly, into engagement with the native tissue as, for example, into engagement with the annulus or native valve leaflets. Stated another way, the pockets act like miniature parachutes around the periphery of the valve. It is expected that pockets 220 will eventually have tissue ingrowth to eliminate the long-term need for their PV leak prevention function. In FIG. 10 the mini-pockets 220 of the cuff are constructed to impede retrograde flow. It will be appreciated, however, that the pockets can be oriented in the opposite direction (i.e., to prevent forward blood flow), with their open sides facing generally proximally. The pockets can be provided in any number, size, and/or shape to minimize leakage. Pockets 220 can be made of the same cuff materials as discussed above.

Figure 11:
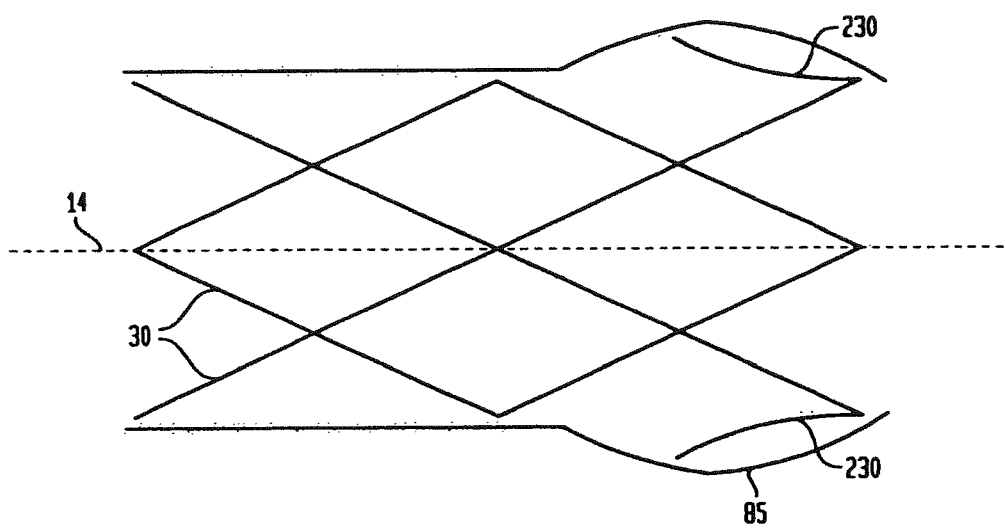
FIG. 11 is a diagrammatic sectional view depicting portions of a valve according to yet another embodiment of the invention.
Figure 12A:
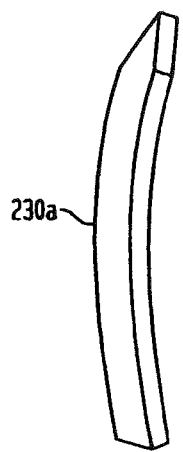
FIGS. 12A and 12B are fragmentary perspective views depicting biasing elements of the valve depicted in FIG. 11, the biasing elements having sharp ends.
Figure 12B:
Figure 12C:
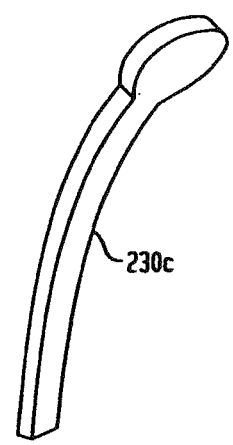
FIGS. 12C and 12D are fragmentary perspective views depicting biasing elements of the valve depicted in FIG. 11, the biasing elements having blunt ends.
Figure 12D:
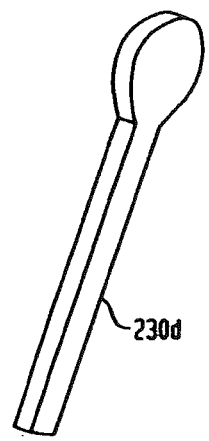

A valve according to a further embodiment of the invention (FIG. 11) incorporates biasing elements in the form of springs 230 formed integrally with the stent body. In the expanded condition of the stent body, portions of the springs project outwardly from the tubular wall of the annulus section 30. The cuff, or the outermost layer of the cuff, is disposed outward of the tubular wall and outward of the springs, so that the springs tend to bias the cuff 85 outwardly with respect to the wall of the annulus section. Biasing elements of this type can be provided at any location along the cuff. The springs 230 may be axially-extensive fingers as depicted in FIG. 12, or may have other configurations. For example, springs in the form of fingers may be directed generally circumferentially. The fingers may have blunt ends for engagement with the cuff, as depicted at 230c and 230d in FIGS. 12C and 12D, respectively. Alternatively, the fingers may have sharp ends as depicted in FIGS. 12A and 12B, respectively, at 230a and 230b. Fingers with sharp ends may pierce the cuff and also may pierce the native tissue.

Figure 13:
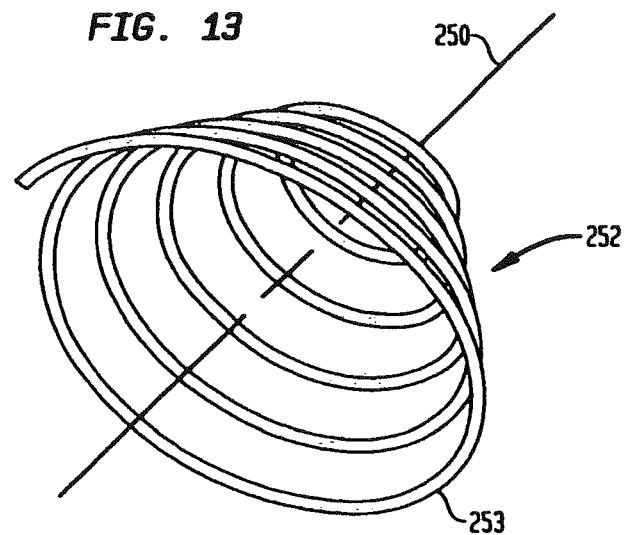
FIG. 13 is a diagrammatic perspective view of a biasing element for use in a further embodiment of the present invention.

The biasing elements may also include coil springs. As shown in FIG. 13, a conical coil spring 252 has a spring axis 250 and a spring member disposed in a helix around the spring axis so that the spring member defines a plurality of turns of progressively increasing diameter. The largest turn 253 defines a base surface of the spring. A plurality of such springs can be mounted between the stent body and the cuff, with the base surface facing inwardly toward the stent body, and with the spring axis extending generally in a radial or outward direction. Here again, the spring will tend to bias the cuff outwardly with respect to the stent body. Where the stent includes cells formed from cell struts, the base surface of each spring may bear on a juncture between struts. Also, where the stent includes commissure posts, such as the posts 50 depicted in FIG. 2, the springs may bear on the commissure posts. In a further arrangement, springs may be provided between layers of a multi-layer cuff. Each spring 252 can be cut from a flat sheet in a coil (spiral) pattern and shaped into a cone. The material can be a shape-memory/super-elastic material such as Nitinol. Depending on the size of the base of the spring, each turn of the spiral could even be saddle-shaped to enable the spring to conform to the curvature of the portion of the stent that the spring is sitting on (FIG. 14).

In a further embodiment (FIG. 14), the turns 251 are generally elliptical as seen in end view, looking along the spring axis 250. Also, in this embodiment, the base surface defined by the largest turn 253 is curved around an axis 257 transverse to the spring axis 250. Thus, portions 255 of turn 253 remote from axis 257 project in directions parallel to the spring axis 250, out of the plane of the drawing, toward the viewer as seen in FIG. 14. The other turns desirably have a similar curvature. Thus, when the spring is fully collapsed, it has the shape of a portion of a cylinder, with axis 257 being the axis of the cylinder. A spring according to this embodiment may be mounted to the stent body, with the transverse axis 257 oriented generally parallel to the axis of the cylindrical surface, and desirably coaxial with such cylindrical surface. Stated another way, the spring in its collapsed or compressed condition may match the curvature of the stent body in its radially collapsed condition. This design has the ability to be low-profile, with minimum radial extent when collapsed, and the ability to push radially outwardly when deployed.

Figure 14:
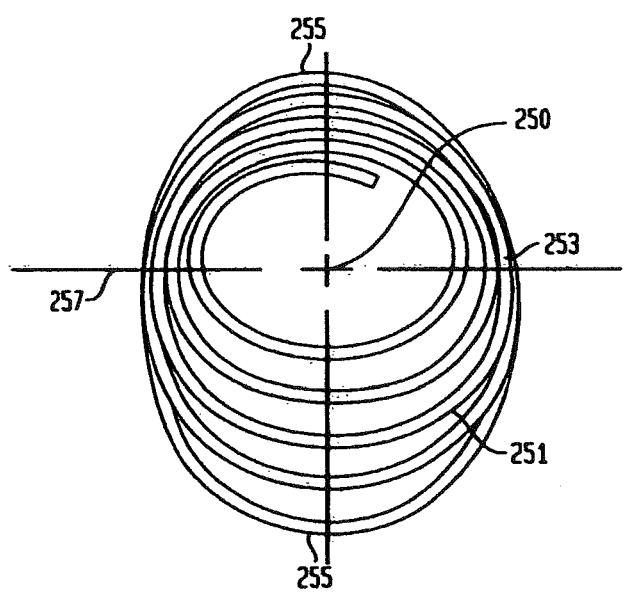
FIG. 14 is a diagrammatic end view of a biasing element used in yet another embodiment of the present invention.

Coil springs as shown in FIGS. 13 and 14 can be cut from a flat sheet, and then heat set or formed on mandrels to make them obtain the characteristics of a spring. They can be attached by means of sutures, welds, locking mechanisms, etc. to the stent body or placed within the appropriate cuff portion. The coil springs also may be formed integrally with the stent body.

Figure 15:
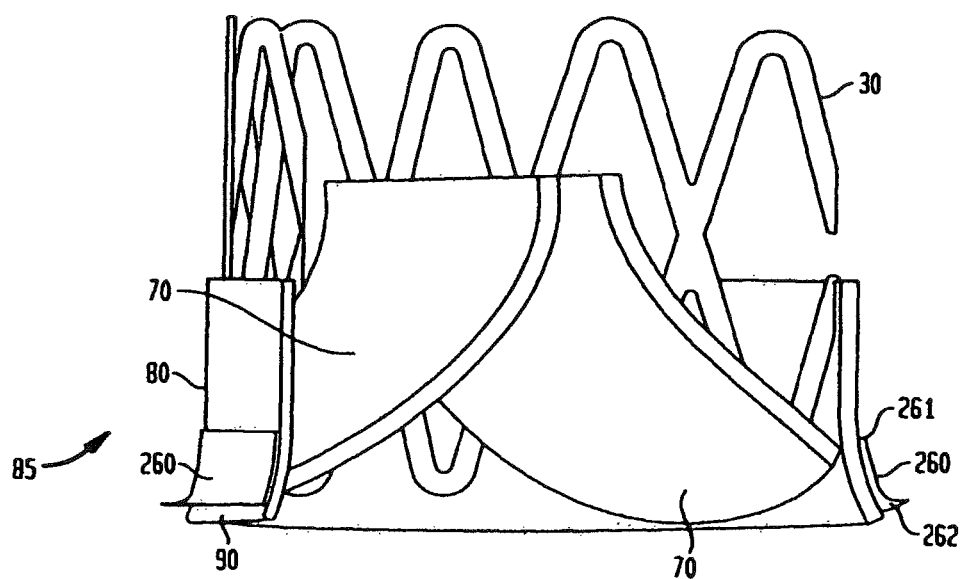
FIG. 15 is a partially sectional view of a valve according to yet another embodiment of the present invention.

A valve according to yet another embodiment of the invention, shown in FIG. 15, includes a cuff 85 similar to the cuffs discussed above. However, in this embodiment, the cuff is provided with a thin ring 260 formed from a resilient material such as silicone rubber. Ring 260 extends circumferentially around the remainder of the cuff and around the annulus section 30 of the stent body. The ring has a main portion 261 bearing on the stent body through the other layers of the cuff, and has a free edge 262 axially offset from the main portion. When the stent body is in its radially collapsed condition, the free edge of the ring lies flat against the other structures of the stent. When the internal diameter of the ring is forcibly expanded by transition of the annulus section 30 of the stent body, the free edge 262 of the ring tends to flip up and thus tends to project outwardly relative to the main portion 261 and relative to the stent body. This causes the free edge 262 of the ring to seal against the surrounding native tissue, even where the native tissue is irregular. The ring has a low enough profile to be collapsed during delivery of the prosthetic valve into the patient. The ring can be placed anywhere along the axial extent of the annulus section. If it is axially offset from the prosthetic valve leaflets 70, as by placing it in the area of the second sub-annular cuff portion 90, this will minimize the material of the valve in the cross section of the leaflets.

Figure 16:
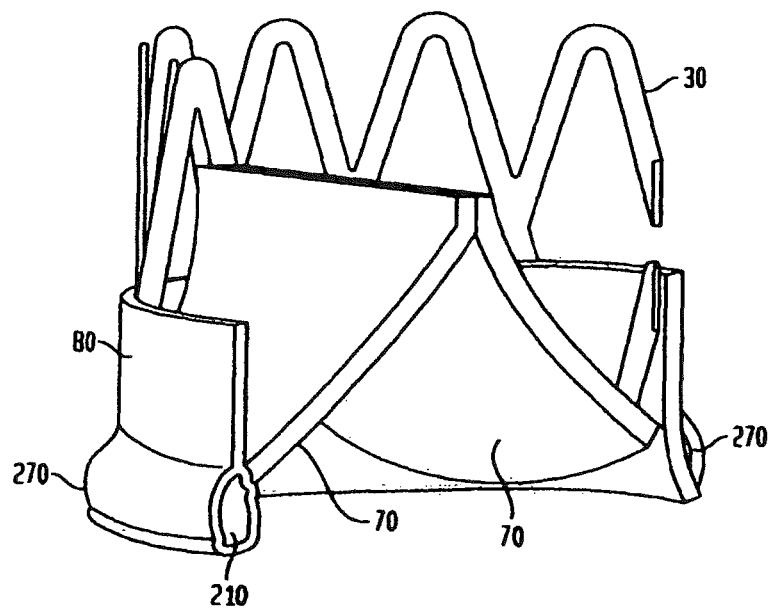
FIG. 16 is a view similar to FIG. 15 but depicting a valve according to a still further embodiment of the present invention.

A ring such as that discussed above with reference to FIG. 15 also can be used as a biasing element, so as to bias another portion of the cuff outwardly with respect to the stent body. For example, in the embodiment of FIG. 16, a ring 260 similar to that discussed above is disposed between the stent body and an overlying portion 270 of cuff material. The free edge of the ring bears on this portion 270 and urges it outwardly with respect to the stent body. The cuff bulge 210 shown in FIG. 16 is thus caused by the free edge of the silicone ring flipping up.

Because the features as discussed above with reference to FIGS. 7-16 provide an outward bias to portions of the cuff, they tend to promote effective sealing between the cuff and the surrounding native tissue even where the native tissue is irregular. While these features have been discussed above in connection with an expansible stent body, they can be used with other types of stents. For example, a valve intended for implantation in an open surgical technique may include a non-expandable, substantially rigid stent. The biasing features may be employed with stents of this type as well.

Figure 17:
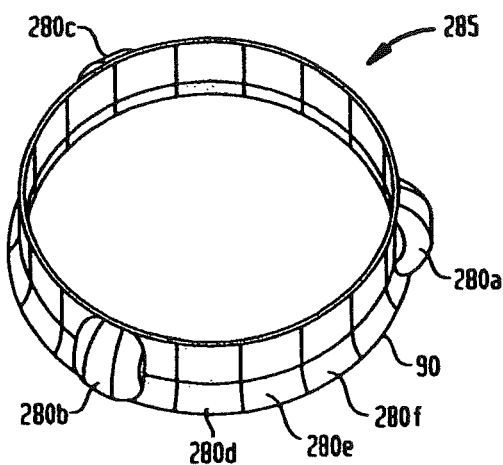
FIG. 17 is a perspective view of a cuff for use in a valve according to a further embodiment of the present invention.
Figure 18:
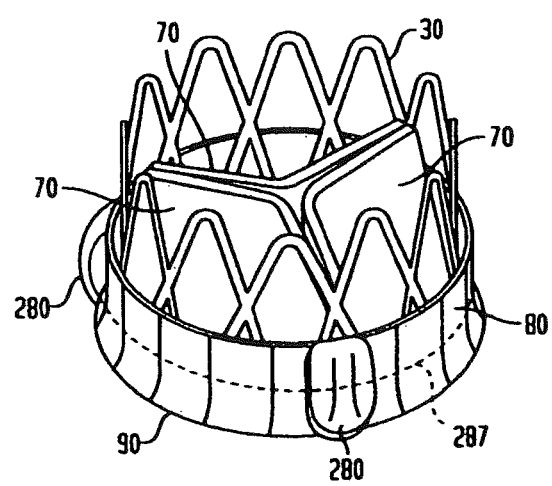
FIG. 18 is a perspective view of a valve incorporating the cuff of FIG. 17.
Figure 19:
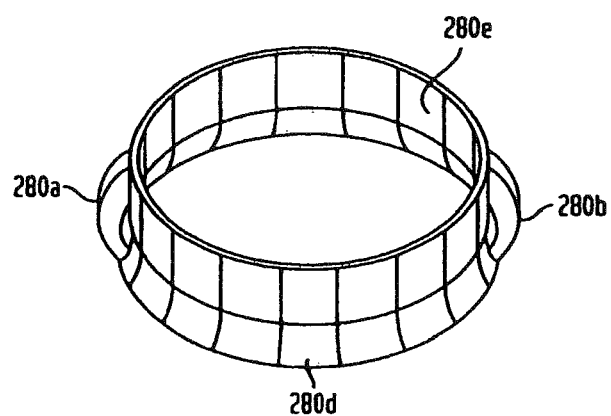
FIG. 19 is a perspective view of another cuff for use in a valve according to yet another embodiment of the present invention.
Figure 20:
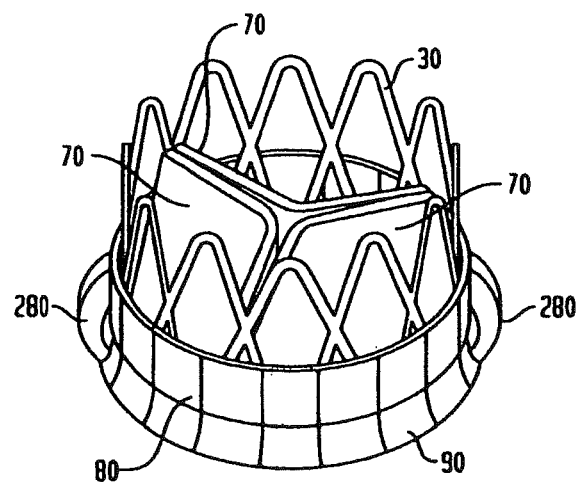
FIG. 20 is a perspective view of a valve utilizing the cuff of FIG. 19.

The calcific patterns of aortic stenosis can occur in a variety of distribution patterns, which can have a direct effect on PV leak between the stenotic leaflets and an implanted collapsible valve. In many cases, PV leak is most likely to occur at the location of the commissures between the stenotic native leaflets (R. Zegdi et al., "Is It Reasonable to Treat All Calcified Stenotic Aortic Valves With a Valved Stent?", Valvular Heart Disease, Vol. 51, No. 5, pp. 579-84, Feb. 5, 2008). Stated another way, the native valve annulus, and the space defined by the interior surfaces of the native valve leaflets, do not have a circular cross-sectional shape. A valve according to a further embodiment includes a cuff 285 (FIG. 17) which includes a plurality of regions 280 distributed around the circumference of the cuff. In the operative, implanted configuration shown, some of these regions 280a, 280b and 280c, referred to herein as "bulge" regions, have a radial thickness R greater than the radial thickness of other regions, such as regions 280d, 280e and 280f, referred to herein as "intermediate" regions. In the particular example of FIGS. 17 and 18, there are three bulge regions spaced circumferentially from one another and intermediate regions between the bulge regions. In another example, shown in FIGS. 19 and 20, there are two bulge regions 280a and 280b spaced from one another and intermediate regions such as 280e and 280d between the bulge regions. The number and location of the bulge regions desirably is selected to match the configuration of the native tissue of the particular patient. Therefore, in order to tailor the valve cuff specifically to a particular patient, each region 280 incorporates a separate chamber 287 (FIG. 18). Each chamber can be inflated to provide a bulge region or left deflated to provide an intermediate region. This arrangement can provide sufficient sealing against PV leak without adding additional, unnecessary cuff material. The configuration of FIGS. 17 and 18 can be used, for example, in a patient having a typical tricuspid native aortic valve with stenotic native leaflets. The configuration of FIGS. 19 and 20 can be used in a patient having a stenotic bicuspid native aortic valve.

The chambers can be inflated either before implantation or after the valve has been expanded into the stenotic native valve. Inflation can be achieved intra-procedurally with material such as liquid collagen or RTV silicone, or prior to the procedure with similar or other materials. This cuff construction offers the potential for a single collapsible valve design to be used in a variety of stenotic aortic valve sizes and calcific distribution patterns, whereas some of the previously known designs can only be used with uniform calcific distribution patterns. This cuff design may also be used in aortic insufficient (leaking) valves because of its ability to fill PV-leaks and gaps. Other possible uses of this cuff design are in other valve positions. For example, a configuration such as that shown in FIGS. 19 and 20 may be particularly well suited for the mitral valve, which is naturally elliptical and often insufficient (leaking).

As further discussed below, certain techniques which can be employed in prosthetic heart valve procedures may best be applied while the regions treated by these techniques are temporarily isolated from direct blood flow. A device that isolates a working chamber may be beneficial. One such device is disclosed in R. Quaden et al., "Percutaneous Aortic Valve Replacement: Resection Before Implantation," European Journal of Cardio-thoracic Surgery, Vol. 27, 2005, pp. 836-40, the disclosure of which is hereby incorporated by reference herein. As disclosed in the Quaden et al. article, an aortic valve resection chamber is sealed by polyethylene balloons. The surgical instruments are inserted through an instrument channel. Two catheters with small sealing balloons provide the coronaries with cardioplegia and prevent coronary embolization during the resection process. A working chamber of this type may also be beneficial (although not necessary in all cases) for application of some techniques such as those described later in this specification.

Lasers have long been used to coagulate tissue in the medical industry. An example is the Laserscope system used for cauterizing tissue (available from Laserscope, 3052 Orchard Drive, San Jose, Calif. 95134-2011). A low power laser that can minimize tissue vaporization, yet bond tissue together, is optimal. Other energy sources such as ultrasound, cryogenics, an electrical resistance or other heating element can be used as alternatives. The cuff of a prosthetic valve can be made to be bonded to native tissue as, for example, to the stenotic leaflets (or to the native valve annulus if leaflets are resected) during or after implantation. For example, a porcine pericardial strip on the outside of the cuff can be used to bond a tissue-to-tissue joint. Probes of various shapes (toroid, pointed, etc.) can be used to directionally apply the energy to the desired locations.

Biocompatible adhesives, such as epoxy amines, have been applied in certain medical applications. (See, for example, U.S. Pat. Nos. 6,780,510 and 6,468,660.) Such adhesives can be applied around the perimeter of the cuff of a prosthetic valve to bond to stenotic leaflets (or annulus if leaflets are resected) during or after implantation. Other silicone materials can be used as a "caulk" in certain situations. The adhesive can be injected internally or externally through ports in the valve cuff itself and/or the cuff can have pockets to allow for injection (see FIGS. 10, 12, and 16.

Figure 21:
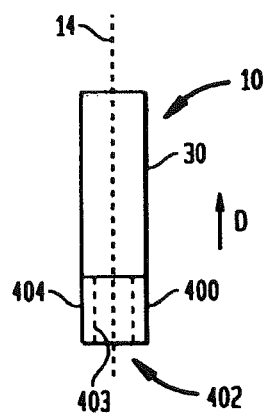
FIG. 21 is an fragmentary diagrammatic elevational view of a collapsed configuration of a valve in accordance with a further embodiment of the present invention.

A valve according to a further embodiment of the invention (FIG. 21) includes an expandable stent body 10 having an annulus section 30 with a proximal-to-distal axis 14. The valve also includes a cuff 400 having a generally tubular wall with a free end 402 and with surfaces 403 and 404. In the collapsed condition shown, surface 403 is the inner surface of the tube and surface 404 is the outer surface. In the radially collapsed condition of the stent body 10, the tubular wall projects from the proximal end of the stent so that the free end 402 of the tubular wall is proximal to the annulus section 30. Stated another way, in this condition, the free end 402 of the tubular wall is axially offset from the annulus section and is axially offset from the stent body. Thus FIG. 21 shows crimped or collapsed stent 30 and crimped or collapsed cuff 400 at different, substantially non-overlapping locations along the proximal-to-distal axis of the valve. Elements 30 and 400 may be connected to one another, e.g., at an interface between them. But they preferably do not overlap, at least not to a great extent. Thus, in this condition the thickness of the tubular wall 400 does not add to the diameter of the stent. This is desirable for keeping the outer diameter, and hence the circumferential size of the valve, as small as possible for less invasive delivery into the patient.

Figure 22:
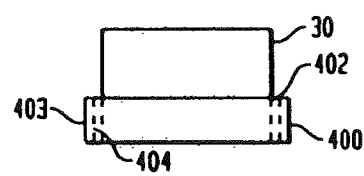
FIG. 22 is a diagrammatic view of the valve of FIG. 21 in a different operating condition.

FIG. 22 shows the structure of FIG. 21 when implanted in the patient. In particular, FIG. 22 shows annulus section 30 in a radially expanded condition. Cuff 400 is also radially expanded and has been flipped up or turned inside-out (everted) so that it is now disposed around the outside of at least a portion of the annulus section 30 of the stent body. Note that surface 403 is now on the outside of the tube. In conversion from the collapsed condition to the operative condition, the free end 402 of the tube moves with respect to the stent body. Accordingly, the free end 402 is referred to herein as a "mobile" portion of the cuff. In the operative condition depicted in FIG. 22, the free end or mobile portion is axially aligned with part of the annulus section 30. In this condition cuff 400 helps ensure proper sealing of the valve to the patient's surrounding native tissue.

Figure 23:
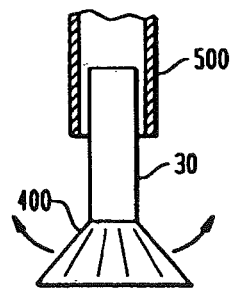
FIG. 23 is a partially sectional diagrammatic view of a valve according to another embodiment of the present invention.
Figure 24:
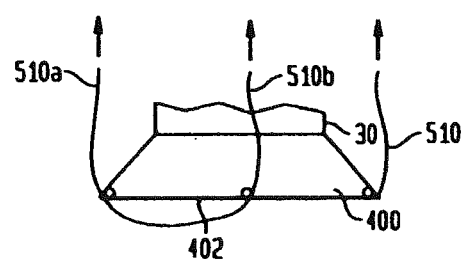
FIG. 24 is a fragmentary schematic view of a valve according to another embodiment of the present invention.
Figure 25:
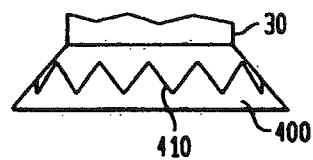
FIG. 25 is a partial, elevational, schematic view of a valve according to a still further embodiment of the present invention.

Tubular cuff 400 can be flipped up during delivery of the valve into the patient but before the valve is fully seated at the valve implant site in the patient. Depending upon the resilient properties of the tubular cuff 400, radial expansion of the stent body may cause the tubular cuff to evert as shown. Alternatively or additionally, the tubular cuff may have a free or undistorted shape such that it naturally tends to evert as shown in FIG. 22 when unconstrained. The tubular cuff may be forcibly distorted to the condition depicted in FIG. 21, and constrained in that position by a sheath or other element of a delivery device. Thus, as shown in FIG. 23, after cuff 400 has emerged from the distal end of a delivery sheath 500, the cuff tends to resiliently flip up around the outside of stent body 10. FIG. 24 shows an alternative or addition in which sutures or wires 510 are used to pull the mobile element or end 402 of cuff 400 up and around the outside of stent body 10. This movement may be performed before, during, or after expansion of the stent body. Merely by way of example, where the delivery device includes an elongated probe, the sutures or wires 510 may extend along the delivery device to a handle or other element accessible to the operator. Also, the sutures may be provided as loops which can be removed from the cuff by selectively pulling one end of the loop. For example, sutures 510a and 510b are parts of a unitary loop extending through holes in the cuff. Pulling both ends of the loop simultaneously tends to pull the free edge or mobile portion 402. Pulling one end of the loop will remove the suture from the cuff. FIG. 25 shows still another alternative or addition in which shape-memory alloy (e.g., nitinol) members 410 in or on cuff 400 cause the cuff to flip up when the cuff is released from delivery system constraint inside the patient at or near the valve implant site.

Figure 26:
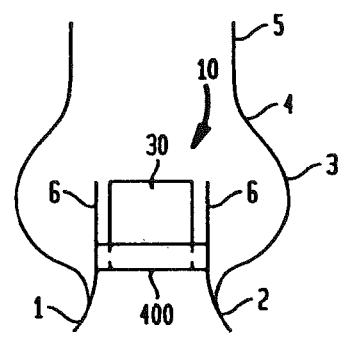
FIG. 26 is a schematic view of a valve according to an embodiment of the present invention in an implanted condition, in conjunction with native tissue.

A cuff with a mobile portion may be arranged to form a seal with any portion of the native anatomy. For example, FIG. 26 shows a prosthetic valve fully implanted in a patient, with cuff 400 flipped up around the outside of stent body 10 and pressed radially outwardly against the patient's native, stenotic, heart valve leaflets 6 to seal the prosthetic valve against PV leak.

Figure 27:
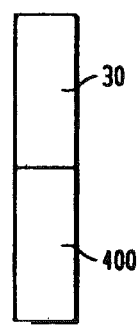
FIG. 27 is a fragmentary, diagrammatic, elevational view of a valve in accordance with yet another embodiment of the present invention.
Figure 28:
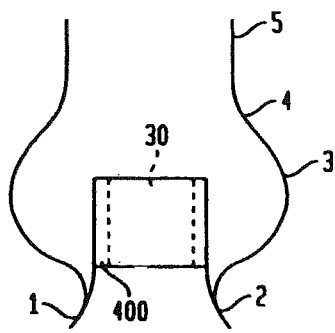
FIG. 28 is a schematic view of the valve of FIG. 27 in an implanted condition, in conjunction with native tissue.

FIG. 27 is generally like FIG. 21, but in FIG. 27, cuff 400 is longer than in FIG. 21. FIG. 28 is generally like FIG. 23, but shows the FIG. 27 structure after it has been implanted in a patient. In the structure of FIGS. 27 and 28, cuff 400 has an axial extent that is about the same as the axial extent of the annulus portion 30 of the stent body. In this embodiment, the proximal end of the stent may be disposed proximal to the native valve annulus 2, and yet a portion of cuff 400 will still reach and seal against native structures such as annulus 2 and stenotic leaflets 6. The structure of FIGS. 27 and 28 incorporates a balloon disposed on the delivery device inside the stent body, such as within the annulus region 30 of the stent body, for forcibly expanding the stent body. This structure also includes a further balloon which is disposed within the cuff when the stent is in the radially collapsed condition. The cuff 400 can be turned inside-out by inflating the second balloon before or during expansion of the stent body. In further variants, the balloon may be arranged to expand progressively, beginning at the free end 402, to help turn the cuff inside out. Merely by way of example, such balloon may include a plurality of chambers disposed along the axis of the structure, so that these chambers can be inflated in sequence.

Figure 29:
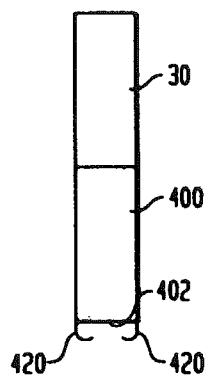
FIG. 29 is a fragmentary, diagrammatic, elevational view of a valve according to a still further embodiment of the present invention.
Figure 30:
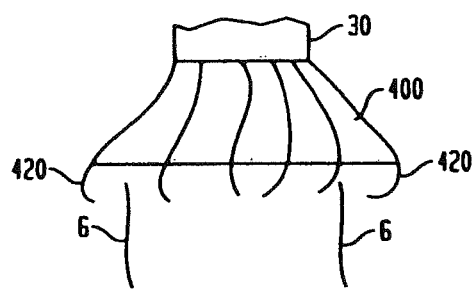
FIG. 30 is a fragmentary schematic view of a portion of the valve of FIG. 30 in a different operating condition.
Figure 31:
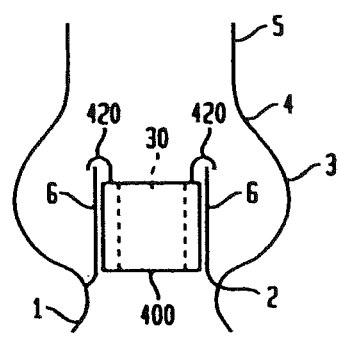
FIG. 31 is a schematic view of the valve of FIGS. 29 and 30 in an implanted condition, in conjunction with native tissue.

In other embodiments, the mobile portion of the cuff may be moved relative to the stent body by engagement with native anatomical structures. For example, the cuff can be constructed and delivered so that it latches on the patient's native stenotic heart valve leaflets during delivery. FIGS. 29-31 show one example of this action. The valve of FIG. 29 is generally similar to the valves of FIGS. 21 and 27, but shows the addition of engagement elements in the form of hooks 420 on the free end 402 of cuff 400 remote from stent 30. FIG. 30 shows the structure of FIG. 29 in a stage of deployment. In this stage, the tubular cuff has deformed to a configuration where the latch members or hooks 420 can engage (latch onto) the distal edges of the patient's native stenotic leaflets 6. Once the latch members have been engaged, the stent body is moved in the proximal direction relative to the native anatomy. As shown in FIG. 31, the proximal movement of stent body 10 into the space bounded by native leaflets 6 causes cuff 400 to evert around the outside of stent 10. This is aided by the fact that hooks 420 secure the free end 402 of cuff 400 to the distal edges of leaflets 6. Ultimately (as shown in FIG. 31), cuff 400 is sandwiched between stent body 10 and native leaflets 6. The presence of hooks 420 over native leaflets 6 helps cuff 400 seal the prosthetic valve against PV leak, and also helps to anchor the valve in place in the patient.

The engagement elements or hooks 420 can be of any suitable material. One possibility is for hooks 420 to be made of nitinol and to extend through the fabric or other material of cuff 400. Hooks 420 may be connected to the annulus section 30 or other portions of the stent body, and may be formed integrally with the stent body.

Figure 32:
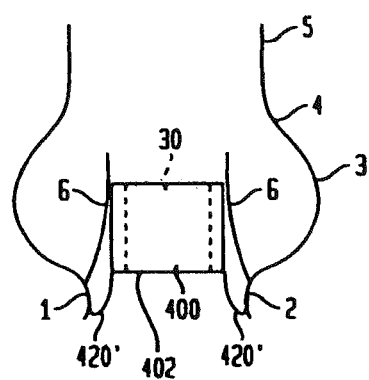
FIG. 32 is a view similar to FIG. 31 but depicting a valve according to a further embodiment of the present invention.

In the procedure of FIGS. 29-31, the mobile element is moved during proximal movement of the valve, from the aorta 5 towards the left ventricle 1. In a further variant, the mobile element is deployed by movement in the opposite, distal direction relative to the native anatomy. In such a case, hooks 420' can be arranged to latch into annulus 2 as shown in FIG. 32. In this arrangement, the tubular cuff element initially projects from the distal end of the annulus section 30. The latch members 420' engage native anatomical structures such as the LVOT. The free end or mobile element moves proximally with respect to the annulus section 30 of the stent body as the stent body moves distally relative to the native anatomy.

The mobile portion of the cuff may include the entire cuff or any part of the cuff. Also, motion of the mobile portion of the cuff can occur in ways other than turning the cuff inside out. For example, the structure of FIG. 33 incorporates a cuff 400 and a stent body 10 having an annulus region 30. During advancement of the valve into the patient, the stent is constrained in its radially collapsed condition by a sheath 605. The cuff 400 includes a resilient tube having an unconstrained internal diameter approximately equal to, or greater than the external diameter of the annulus region 30 in its radially collapsed condition. During advancement into the patient, the cuff is retained in a collapsed condition by a further sheath 607 separate from sheath 605. During deployment, sheath 607 is moved in axial direction A1 relative to sheath 605, so as to free at least the part of cuff 400 closest to the stent body and allow it to expand. While moving sheath 605 axially in direction A2 relative to the stent body, the cuff is also moved axially relative to the stent body before the stent body expands fully to its operative, radially expanded state. For example, the delivery device may include sutures 510 similar to those discussed above with reference to FIG. 24 for moving the cuff. As the stent body expands, it engages the inside of the cuff. Where the stent body is forcibly expanded by a balloon or mechanical element, the cuff can be slipped over the exterior of the stent body so as to pull the cuff around the outside of the stent body before or during operation of the expansion device.

Although the valves have been discussed above with reference to implantation of the valves in naturally-occuring native valves of a patient, the valves also can be implanted within previously-implanted prosthetic valves. In such a procedure, the previously-implanted prosthetic valve constitutes the native valve. For example, the cuff will seal against structures of the previously-implanted prosthetic valve as, for example, against the interior of the previously-implanted stent body and cuff, or the interior surfaces of previously-implanted prosthetic valve leaflets.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve for replacement of a native heart valve having a native valve annulus, comprising:
    (a) a stent body having a proximal end and a distal end and including a generally tubular annulus region and a flare section proximal to the annulus region, the stent body having a proximal-to-distal axis, a radially collapsed condition, and an unconstrained, fully radially expanded condition, the annulus region and the flare section increasing in diameter during transition from the radially collapsed condition to the radially expanded condition, the flare section extending from the annulus region to the proximal end of the stent, the flare section having a diameter which increases progressively in the proximal direction over the entire flare section from a diameter equal to a diameter of the annulus region at a juncture between the annulus region and the flare section to a diameter at the proximal end of the stent greater the diameter of the annulus region when the stent body is in the unconstrained, fully radially expanded condition, wherein the stent body further includes an aortic section distal to the annulus region, the aortic section having a larger diameter than a proximalmost end of the stent when the stent body is in the unconstrained, fully radially expanded condition, wherein in the unconstrained, fully radially expanded condition of the stent body, an ablumenal surface of the flare section is continuously concave from the annulus region to the proximalmost end of the stent;
    (b) one or more prosthetic valve elements mounted to the stent body and operative to allow flow in the antegrade direction through the annulus region but to substantially block flow in the retrograde direction through the annulus region; and
    (c) a cuff secured to the stent body, the cuff comprising
        (i) a first cuff portion covering at least a portion of an exterior surface of the annulus region for disposition at the native valve annulus, the first cuff portion having a substantially constant first diameter when the stent body is in the unconstrained, fully radially expanded condition, and
        (ii) a second cuff portion proximal to the first cuff portion and integral with the first cuff portion, at least a part of the second cuff portion extending along an exterior surface of the flare section of the stent body, the second cuff portion having a diameter which increases progressively in the proximal direction to a second diameter when the stent body is in the radially expanded condition, the second diameter being greater than the first diameter, the second cuff portion being adapted for engagement with native tissue proximal to the native valve annulus.

2. A valve as claimed in claim 1, wherein the one or more valve elements include a plurality of flexible prosthetic valve leaflets disposed at least partially within the annulus region.

3. A valve as claimed in claim 2, wherein the plurality of leaflets are secured to the cuff along leaflet bases, at least a part of the second cuff portion extending between the leaflet bases and a proximal edge of the cuff.

4. A valve as claimed in claim 1, wherein the stent is fully self-expanding.

5. A valve as claimed in claim 1, wherein the aortic section has a larger diameter than the annulus region when the stent body is in the unconstrained, fully radially expanded condition.

6. A valve as claimed in claim 1, wherein the stent body includes a transition section between the annulus region and the aortic section, an ablumenal surface of the transition section being continuously concave from the annulus region to the aortic region in the unconstrained, fully radially expanded condition of the stent body.

* * * * *